US010966628B2

(12) United States Patent
Takeuchi et al.

(10) Patent No.: US 10,966,628 B2
(45) Date of Patent: Apr. 6, 2021

(54) ULTRASOUND DIAGNOSIS APPARATUS

(71) Applicant: Toshiba Medical Systems Corporation, Otawara (JP)

(72) Inventors: Takashi Takeuchi, Otawara (JP); Yusuke Kobayashi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 1106 days.

(21) Appl. No.: 14/921,178

(22) Filed: Oct. 23, 2015

(65) Prior Publication Data

US 2016/0135789 A1 May 19, 2016

(30) Foreign Application Priority Data

Nov. 19, 2014 (JP) .............................. JP2014-234316

(51) Int. Cl.
*A61B 5/055* (2006.01)
*A61B 8/00* (2006.01)
(Continued)

(52) U.S. Cl.
CPC ............ *A61B 5/055* (2013.01); *A61B 8/5261* (2013.01); *A61B 8/54* (2013.01); *A61B 6/032* (2013.01);
(Continued)

(58) Field of Classification Search
CPC ......... A61B 8/54; A61B 8/5261; A61B 5/055; A61B 6/032; A61B 8/145; A61B 8/0875;
(Continued)

(56) References Cited

U.S. PATENT DOCUMENTS 4,917,097 A * 4/1990 Proudian .................. A61B 8/12
600/463
2004/0006272 A1* 1/2004 Vortman .............. A61B 8/5276
600/443
(Continued)

FOREIGN PATENT DOCUMENTS

JP 5-146445 6/1993
JP 2006-158413 A 6/2006
(Continued)

OTHER PUBLICATIONS

Vignon et al. 2006 J. Acoust. Soc. Am. 120:2737-2745.*
(Continued)

*Primary Examiner* — Keith M Raymond
*Assistant Examiner* — Patrick M Mehl
(74) *Attorney, Agent, or Firm* — Oblon, McClelland, Maier & Neustadt, L.L.P.

(57) ABSTRACT

According to one embodiment, an ultrasound diagnosis apparatus is configured to generate ultrasound image data of a subject through an ultrasound probe. The ultrasound diagnosis apparatus includes a specifying unit, a transmission/reception condition change unit, and an image generator. The specifying unit specifies a characteristic site, which is included in a scanning range related to the ultrasound image data and has specific acoustic characteristics, based on three-dimensional image data of the subject generated in advance. The transmission/reception condition change unit changes transmission/reception conditions of ultrasound waves based on the acoustic characteristics of the characteristic site. The image generator generates the ultrasound image data based on changed transmission/reception conditions.

12 Claims, 13 Drawing Sheets

(51) Int. Cl.
*A61B 8/08* (2006.01)
*A61B 6/03* (2006.01)
*A61B 8/14* (2006.01)

(52) U.S. Cl.
CPC .............. *A61B 8/0875* (2013.01); *A61B 8/145* (2013.01); *A61B 8/4254* (2013.01); *A61B 8/4494* (2013.01)

(58) Field of Classification Search
CPC ....... A61B 8/4254; A61B 8/4494; A61B 8/00; A61B 8/0808; A61B 8/5284; A61B 8/5292
See application file for complete search history.

(56) References Cited

U.S. PATENT DOCUMENTS

| | | | | |
|---|---|---|---|---|
| 2005/0004461 | A1* | 1/2005 | Abend | G01S 7/52026 600/437 |
| 2008/0110263 | A1* | 5/2008 | Klessel | G01S 7/52085 73/602 |
| 2010/0268088 | A1* | 10/2010 | Prus | A61B 8/14 600/459 |
| 2011/0172538 | A1* | 7/2011 | Sumi | A61B 8/463 600/453 |
| 2012/0165670 | A1* | 6/2012 | Shi | A61B 8/481 600/442 |
| 2012/0253171 | A1 | 10/2012 | Ishikawa et al. | |
| 2014/0147027 | A1 | 5/2014 | Jain et al. | |
| 2016/0187473 | A1* | 6/2016 | Maev | A61B 8/0816 600/442 |

FOREIGN PATENT DOCUMENTS

| | | |
|---|---|---|
| JP | 2012-213557 A | 11/2012 |
| JP | 2014-161478 A | 9/2014 |
| WO | WO 2013/005136 A1 | 1/2013 |

OTHER PUBLICATIONS

Price and Links, Ultrasound Imaging System in: Medical Imaging Signals and Systems, Price & Links Edts, Pearson & Prentice Hall, 1st Edition 2005, Chap.11, p. 347-378.*
Lindsey et al. 2014 Ultrasonic Imaging 36:35-54 (Year: 2013).*
Clement et al. 2002 Phys. Med. Biol. 47:1219-36 (Year: 2002).*
O'Reilly et al. 2013 Med. Phys. 40:110701-1-110701-7 (Year: 2013).*
Huang et al. 2012 J. Biomed. Optics 17:066016-1-066016-8 (Year: 2012).*
Office Action dated Jun. 5, 2018 in Japanese Patent Application No. 2014-234316.

* cited by examiner

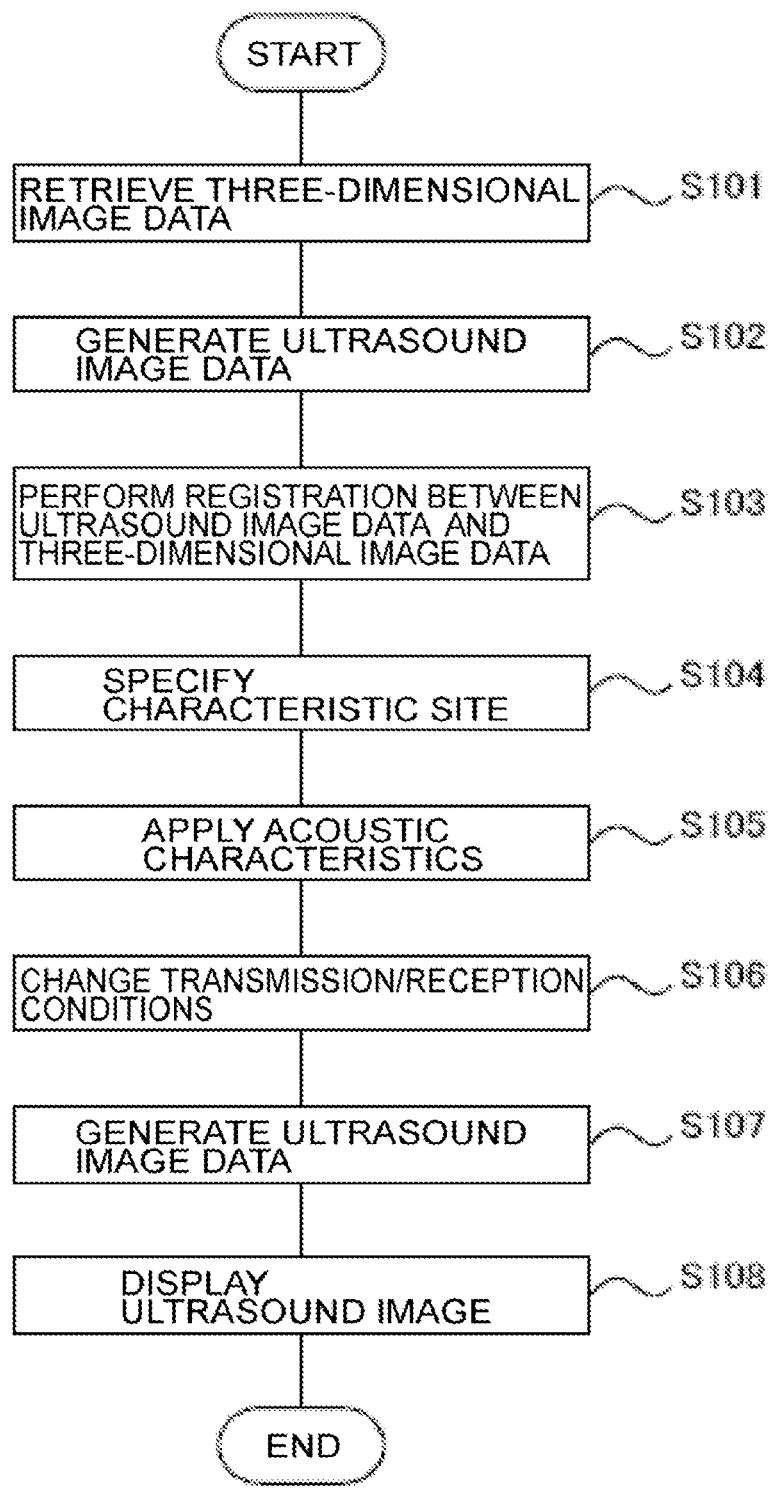

ULTRASOUND DIAGNOSIS APPARATUS

CROSS-REFERENCE TO RELATED APPLICATION

This application is based upon and claims the benefit of priority from Japanese Patent Application No. 2014-234316, filed Nov. 19, 2014; the entire contents of which are incorporated herein by reference.

FIELD

Embodiments described herein relate generally to an ultrasound diagnosis apparatus.

BACKGROUND

An ultrasound diagnosis apparatus transmits ultrasound waves to a subject and receives reflected waves therefrom via an ultrasound probe to thereby acquire biological information of a subject. The ultrasound diagnosis apparatus generates an ultrasound image that represents, for example, the tissue structure of the subject based on the biological information.

The ultrasound diagnosis apparatus may be used to generate an ultrasound image of the brain by transmitting ultrasound waves through the skull and receiving reflected waves therefrom. The skull has acoustic characteristics, such as acoustic velocity and attenuation rate, largely different from those of other sites. If a range (scanning range) where ultrasound waves are transmitted and received includes tissue, such as bone, having acoustic characteristics largely different from those of other sites, the ultrasound waves are refracted by the tissue (sound field is disturbed). The same applies to the case where ultrasound waves are transmitted and received with respect to the ribs, the knee, the elbow, and the like. Besides, the shape of the tissue varies depending on the subject. This reduces the image quality of ultrasound images.

BRIEF DESCRIPTION OF THE DRAWINGS

FIG. 4 is a flowchart of the operation of the ultrasound diagnosis apparatus of the first embodiment;

DETAILED DESCRIPTION

Figure 1:
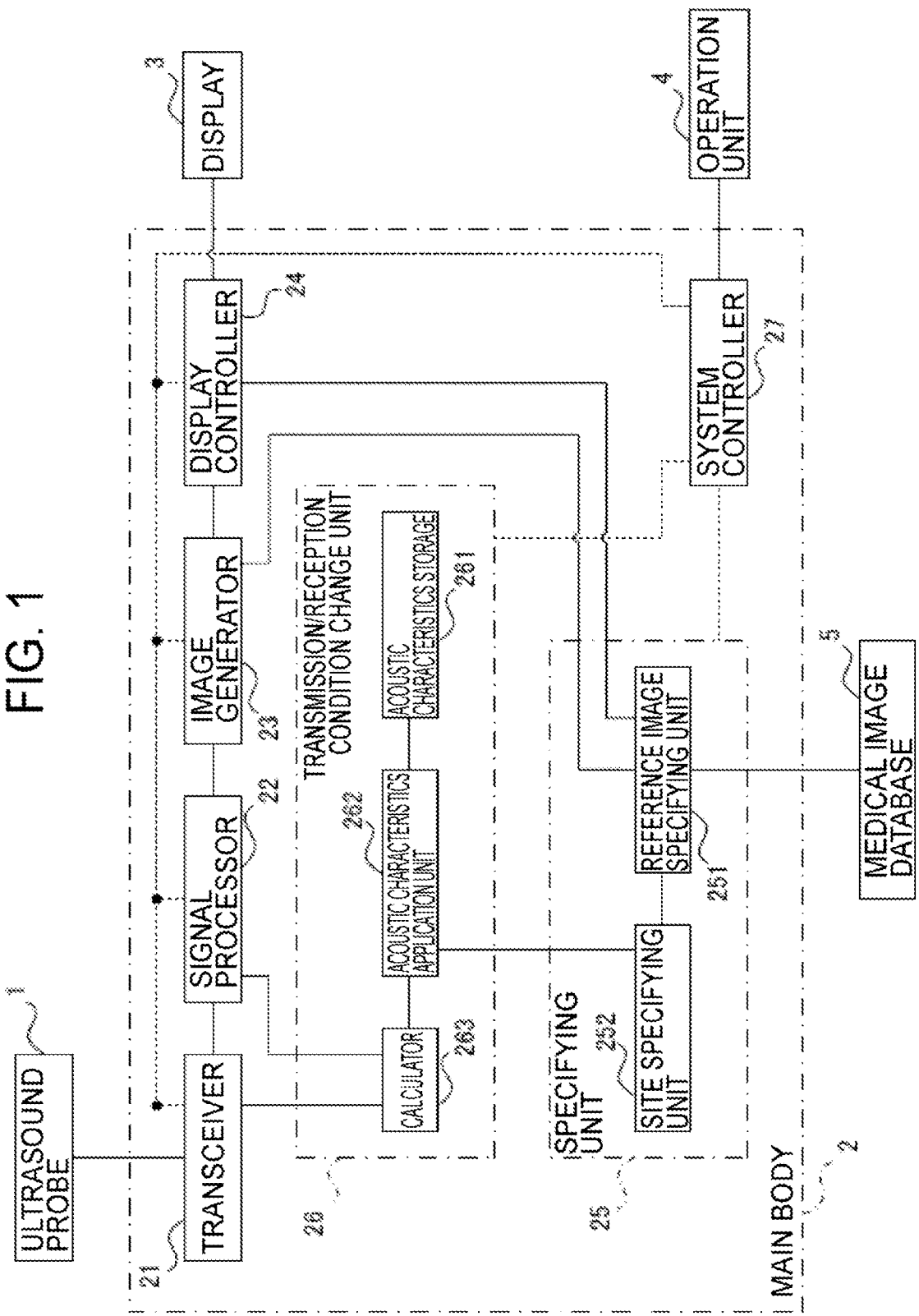
FIG. 1 is a block diagram illustrating the configuration of an ultrasound diagnosis apparatus according to a first embodiment.

In general, according to one embodiment, an ultrasound diagnosis apparatus is configured to generate ultrasound image data of a subject through an ultrasound probe. The ultrasound diagnosis apparatus includes a specifying unit, a transmission/reception condition change unit, and an image generator. The specifying unit specifies a characteristic site, which is included in a scanning range related to the ultrasound image data and has specific acoustic characteristics, based on three-dimensional image data of the subject generated in advance. The transmission/reception condition change unit changes transmission/reception conditions of ultrasound waves based on the acoustic characteristics of the characteristic site. The image generator generates the ultrasound image data based on changed transmission/reception conditions.

Referring now to the drawings, a description is given of an ultrasound diagnosis apparatus according to embodiments.

First Embodiment

FIG. 1 is a block diagram illustrating the configuration of an ultrasound diagnosis apparatus according to a first embodiment. The ultrasound diagnosis apparatus of the first embodiment is configured to generate an ultrasound image of a subject through an ultrasound probe 1. The ultrasound diagnosis apparatus includes the ultrasound probe 1, a main body 2, a display 3, and an operation unit 4. The main body 2 is communicably connected to a medical image database 5.

The medical image database 5 stores three-dimensional image data of a subject. The three-dimensional image data is generated in advance by a medical image diagnosis apparatus such as, for example, an X-ray diagnosis apparatus, an X-ray computed tomography (CT) apparatus, a magnetic resonance imaging (MRI) apparatus, or an ultrasound diagnosis apparatus using a two-dimensional array probe. The medical image database 5 constitutes, for example, a system conforming to the Digital Imaging and Communications in Medicine (DICOM) standard. The main body 2 may be communicably connected to a medical image diagnosis apparatus such as an X-ray diagnosis apparatus, an X-ray CT apparatus, an MRI apparatus, or another ultrasound diagnosis apparatus, instead of the medical image database 5.

The ultrasound probe 1 transmits ultrasound waves to a subject and receives the waves reflected from the subject. The ultrasound probe 1 outputs an echo signal that represents the reflected waves to a transceiver 21. The ultrasound probe 1 includes a plurality of ultrasound transducers. The ultrasound probe 1 may be a one-dimensional array probe in which the ultrasound transducers are arranged in an array in the operation direction, or a two-dimensional array probe in which the ultrasound transducers are arranged in two-dimensional arrays.

The main body 2 includes the transceiver 21, a signal processor 22, an image generator 23, a display controller 24, a specifying unit 25, a transmission/reception condition change unit 26, and a system controller 27. The transceiver 21 outputs a pulse signal to the ultrasound probe 1 to make the transceiver 21 transmit ultrasound waves. The transceiver 21 includes a pulser with respect to each channel that corresponds to each of the ultrasound transducers, and outputs a pulse signal at a timing delayed for each channel. Thereby, the transceiver 21 transmits ultrasound waves subjected to beam forming (transmission beam forming) to a predetermined focus. The delay time is calculated based on a positional relationship between one of the ultrasound transducers corresponding to the channel and the focus. The transmission beam forming is performed with respect to each focus included in the scanning range of ultrasound waves.

Besides, the transceiver 21 receives the echo signal from each of the ultrasound transducers of the ultrasound probe 1. The transceiver 21 includes a common preamplifier circuit and an analog-to-digital (A/D) converter circuit. The preamplifier circuit amplifies the echo signal received from the ultrasound probe 1 with respect to each channel, and outputs it to the A/D converter circuit. The A/D converter circuit converts the echo signal amplified by the preamplifier circuit to a digital signal (reception signal) with respect to each channel, and outputs it to the signal processor 22.

Figure 2:
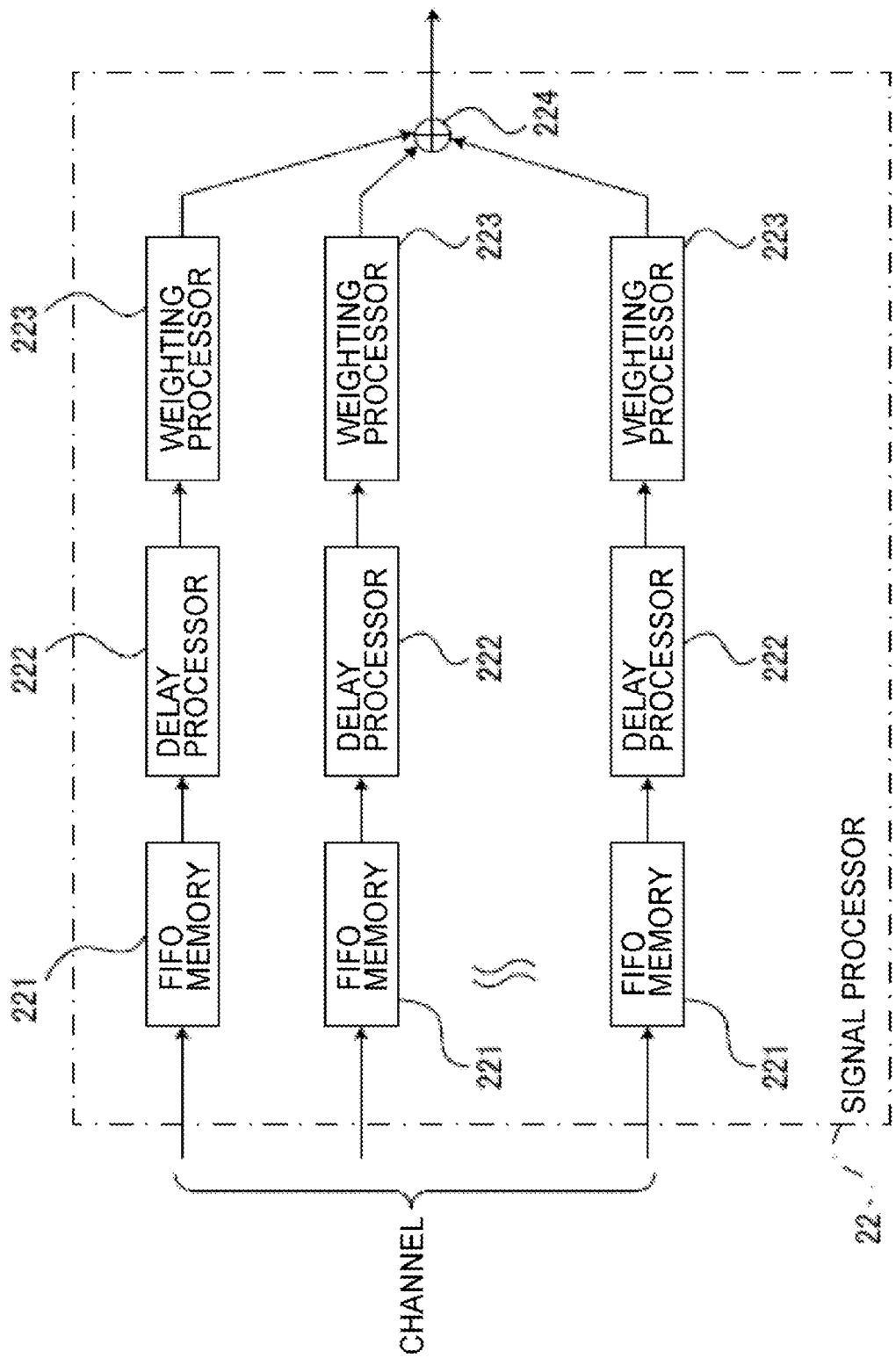
FIG. 2 is a block diagram illustrating the configuration of a signal processor of the first embodiment.

The signal processor 22 performs delay processing and addition processing on the reception signal from the transceiver 21 to obtain the reception signal subjected to phasing (reception beam forming). FIG. 2 is a block diagram illustrating the configuration of the signal processor 22 of the first embodiment. The signal processor 22 includes first-in first-out (FIFO) memories 221, delay processors 222, weighting processors 223, and an adder 224.

The FIFO memory 221 is provided to each channel. The FIFO memory 221 receives the reception signal from the transceiver 21 and stores it.

The delay processor 222 is provided to each channel. The delay processor 222 retrieves the reception signal from the FIFO memory 221. At this time, the delay processor 222 retrieves the reception signal stored in an address corresponding to the delay time. The retrieval of the reception signal from the address corresponds to the addition of the delay time to the reception signal. The delay time is calculated based on a positional relationship between one of the ultrasound transducers corresponding to the channel and the focus. The delay processor 222 outputs the reception signal retrieved to the weighting processor 223.

Incidentally, the delay processor 222 may include a common small delay circuit. The small delay circuit further adds a delay time, which is less than the clock rate of the FIFO memory 221, to the reception signal.

The weighting processor 223 is provided to each channel. The weighting processor 223 multiplies the reception signal received from the delay processor 222 by a weighting coefficient. The weighting coefficient is obtained based on a positional relationship between one of the ultrasound transducers corresponding to the channel and the focus. The weighting processor 223 outputs the reception signal multiplied by the weighting coefficient to the adder 224.

The adder 224 receives the reception signal from each of the weighting processors 223, and adds them up. This addition obtains the reception signal subjected to reception beam forming with respect to a predetermined focus. The adder 224 outputs the reception signal subjected to reception beam forming to the image generator 23.

Note that the delay processors 222, the weighting processors 223, and the adder 224 perform above process with respect to each focus included in the scanning range of ultrasound waves.

The image generator 23 generates ultrasound image data based on the reception signal from the signal processor 22. For example, having received the reception signal from the signal processor 22, the image generator 23 visualizes a parameter for the amplitude of the reception signal. At this time, the image generator 23 performs band-pass filtering on the reception signal, and detects the envelope of the reception signal after the band-pass filtering. The image generator 23 then performs logarithmic transformation filtering on the detected data to generate ultrasound raster data that represents a tomographic image of the subject.

The image generator 23 generates ultrasound image data based on the ultrasound raster data. The image generator 23 includes, for example, a digital scan converter (DSC). The image generator 23 scan-converts data represented by a signal sequence of each scan line in the ultrasound raster data to ultrasound image data represented by display coordinates. The image generator 23 generates the ultrasound image data (B-mode image data) that represents a tomographic image of the subject, and outputs it to the display controller 24 and the specifying unit 25.

While an example is mainly described in which the image generator 23 generates the ultrasound image data that represents a tomographic image of the subject, it may generate data that represents blood flow information of the subject. For example, the image generator 23 may obtain Doppler shift frequency component by phase detection of the reception signal, and perform fast Fourier transform (FFT) thereon to generate Doppler frequency distribution data that represents the blood flow velocity. Besides, the image generator 23 may generate color flow mapping (CFM) image data that represents the velocity, distribution, and power of the blood flow.

Upon receipt of the ultrasound image data from the image generator 23, the display controller 24 displays, on the display 3, an ultrasound image based on the ultrasound image data.

The display 3 displays the ultrasound image. The display 3 includes a display device such as, for example, liquid crystal display (LCD), organic electroluminescent (EL) display, or the like.

The specifying unit 25 specifies a characteristic site, which is included in a scanning range related to the ultrasound image data and has specific acoustic characteristics. The specifying unit 25 includes a reference image specifying unit 251 and a site specifying unit 252.

The reference image specifying unit 251 retrieves the three-dimensional image data of the subject generated in advance from the medical image database 5. Besides, the reference image specifying unit 251 receives the ultrasound image data from the image generator 23. For example, the reference image specifying unit 251 extracts three or more pixels having a brightness value equal to or above a predetermined threshold from the ultrasound image data as characteristic points. The predetermined threshold is designed as appropriate. In addition, the reference image specifying unit 251 extracts three or more pixels having a brightness value equal to or above a predetermined threshold from the three-dimensional image data as characteristic points. The predetermined threshold is designed as appropriate. The reference image specifying unit 251 performs registration or position matching between the characteristic points extracted from the ultrasound image data and those extracted from the three-dimensional image data. This achieves registration between the three-dimensional image data and the ultrasound image data. Thus, the coordinate system of the ultrasound image data, i.e., the coordinate system of the scanning range of ultrasound waves, corresponds to the coordinate system of the three-dimensional image data.

The reference image specifying unit 251 specifies, as reference image data, image data having a plane of the ultrasound image data as a cross section in the three-dimensional image data by multi-planar reconstruction (MPR). When the ultrasound probe 1 is a two-dimensional array probe, the reference image specifying unit 251 specifies, as reference image data, image data that contains partial data corresponding to the range of the ultrasound image data from the three-dimensional image data. The reference image specifying unit 251 outputs the reference image data thus specified and the ultrasound image data to the site specifying unit 252. Alternatively, the reference image specifying unit 251 may output the reference image data to the display controller 24.

The site specifying unit 252 specifies a characteristic site, which is included in a scanning range related to the ultrasound image data and has specific acoustic characteristics, in the reference image data. The characteristic site having specific acoustic characteristics refers to a site with acoustic characteristics, such as acoustic velocity and attenuation rate, largely different from those of other sites. Examples of the characteristic site include hard tissue site such as bone. For example, the site specifying unit 252 extracts a site having specific acoustic characteristics from the reference image data. At this time, the site specifying unit 252 extracts a group of pixels having a brightness value equal to or above a predetermined threshold from the reference image data. Then, the site specifying unit 252 identifies the sites of the group of pixels extracted. In general, the characteristic site is represented by pixels with higher brightness as compared to other sites in the reference image data (the partial data of the three-dimensional image data retrieved). The operator provides, in advance, a value for extracting the characteristic site as the predetermined threshold.

The site specifying unit 252 correlates the sites of the group of pixels extracted (site having specific acoustic characteristics) with the scanning range related to the ultrasound image data, thereby specifying a site included in the scanning range from among the sites of the group of pixels as the characteristic site. With this, the position and the shape of the characteristic site included in the scanning range are specified. The site specifying unit 252 outputs characteristic site data that represents the position and the shape of the characteristic site thus specified and the ultrasound image data to the transmission/reception condition change unit 26.

The transmission/reception condition change unit 26 changes the transmission/reception conditions of ultrasound waves based on the acoustic characteristics of the characteristic site specified. The transmission/reception condition change unit 26 includes an acoustic characteristics storage 261, an acoustic characteristics application unit 262, and a calculator 263.

The acoustic characteristics storage 261 stores in advance acoustic characteristics of the characteristic site per unit length. For example, the acoustic characteristics storage 261 stores in advance clinically known acoustic velocity and attenuation rate per unit length of the site such as bone. The acoustic characteristics storage 261 may further store the density of the characteristic site in advance. The operator provides in advance values of the acoustic characteristics per unit length.

The acoustic characteristics application unit 262 receives the characteristic site data and the ultrasound image data from the site specifying unit 252. The acoustic characteristics application unit 262 retrieves the acoustic characteristics per unit length from the acoustic characteristics storage 261. The acoustic characteristics application unit 262 applies (reflects) the acoustic characteristics per unit length to the position (the position of the characteristic site) represented by the characteristic site data. This specifies the position and the shape of the characteristic site to which the acoustic characteristics of the characteristic site are applied (reflected) in the scanning range represented by the ultrasound image data. The acoustic characteristics application unit 262 outputs acoustic characteristics application data, in which the acoustic characteristics of the characteristic site are applied to the scanning range of the ultrasound image data, to the calculator 263.

The calculator 263 calculates the transmission/reception conditions to be changed based on the acoustic characteristics application data from the acoustic characteristics application unit 262. Examples of the transmission/reception conditions include the delay time for each channel related to the transmission/reception of ultrasound waves and the weighting coefficient for each channel used by the weighting processor 223.

Figure 3A:
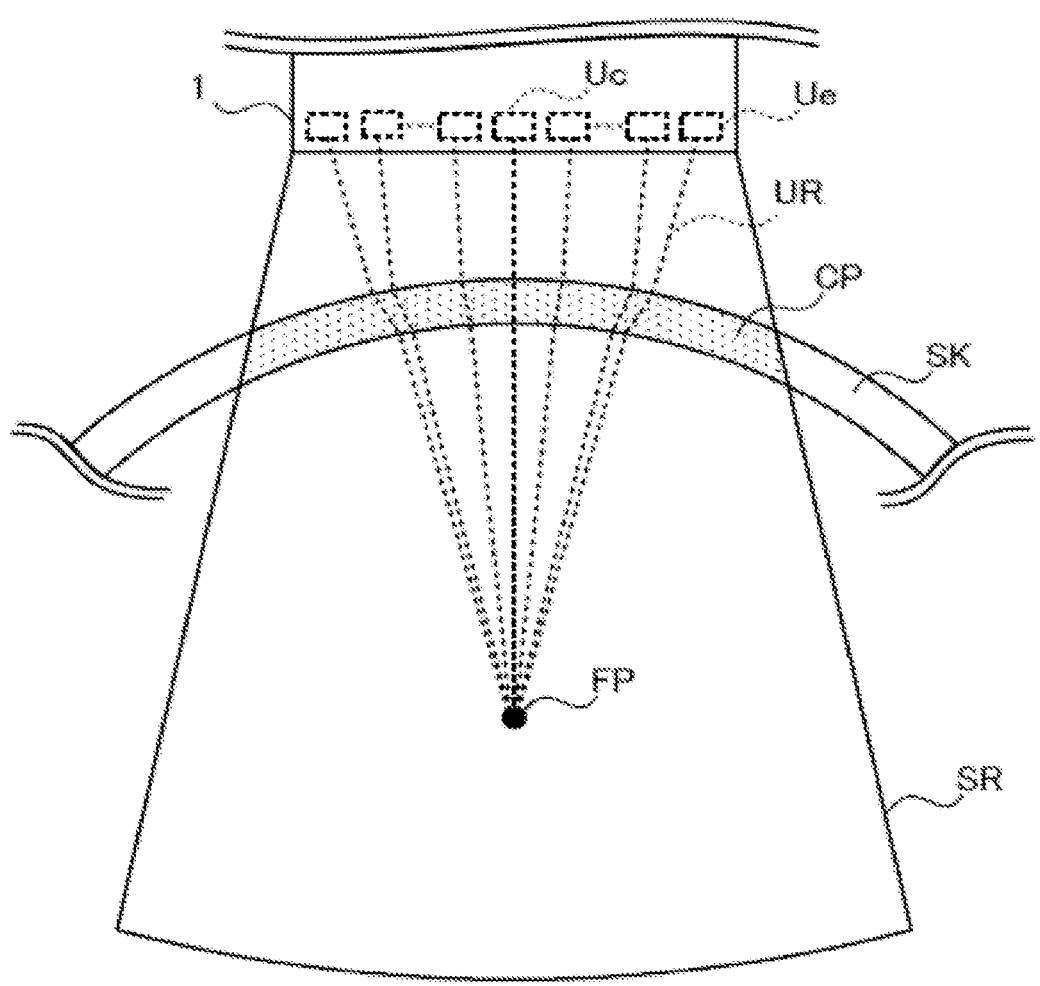
FIG. 3A is a schematic diagram schematically illustrating acoustic characteristics application data of the first embodiment.
Figure 3B:
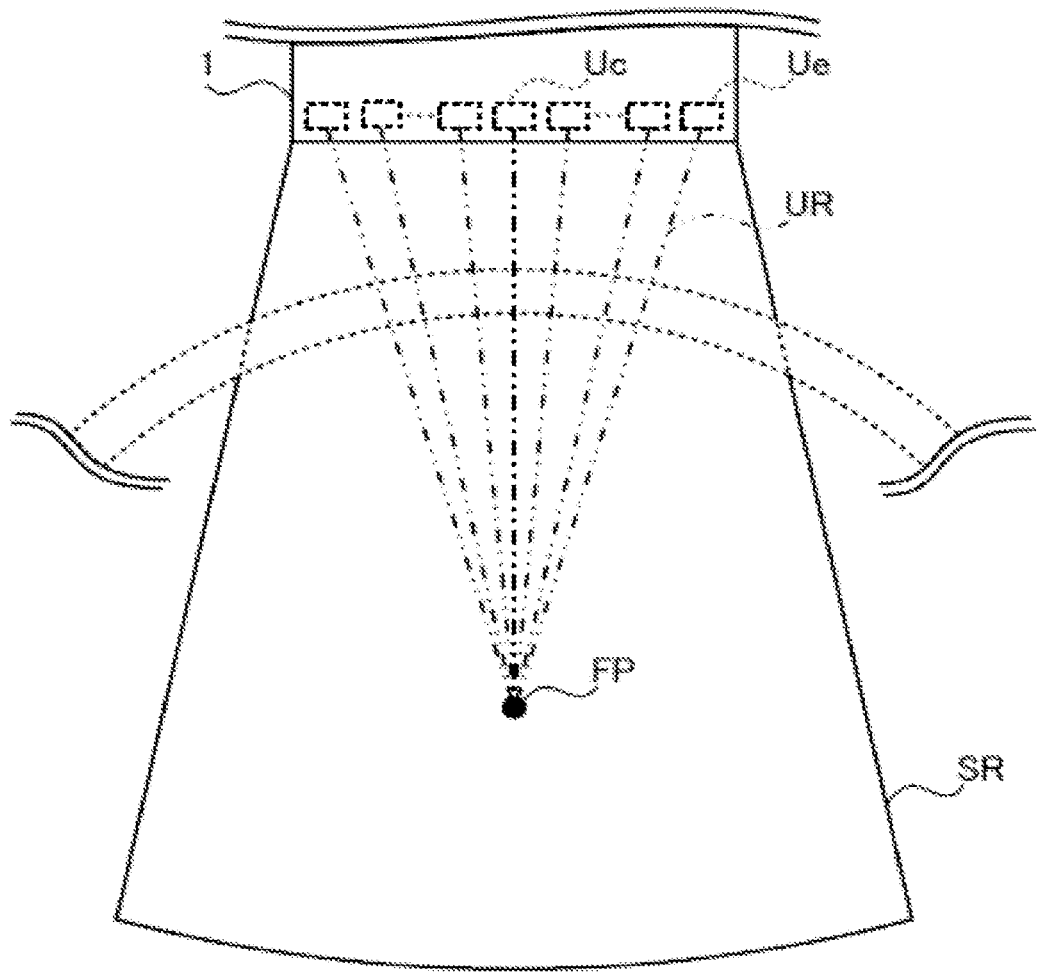
FIG. 3B is a schematic diagram schematically illustrating a sound field where acoustic characteristics of a characteristic site are not applied in the first embodiment.

FIG. 3A is a schematic diagram schematically illustrating the acoustic characteristics application data of the first embodiment. Described below is transmission/reception of ultrasound waves between one focal point FP in a scanning range SR and an ultrasound transducer U (Uc, Ue) of the ultrasound probe 1. In the example of FIG. 3A, the scanning range SR includes a part of the skull SK of the subject as a characteristic site CP. FIG. 3B is a schematic diagram schematically illustrating a sound field where acoustic characteristics of a characteristic site are not applied in the first embodiment.

General transmission/reception conditions are determined in advance such that the acoustic velocity and the attenuation rate are uniform in the scanning range. In this case, as an example of FIG. 3B, the delay time and the weighting coefficient are determined based on a linear positional relationship between the focal point and each of the ultrasound transducers. Meanwhile, as an example of FIG. 3A, when the scanning range SR includes the characteristic site CP, ultrasound waves are transmitted/received between the focal point and each of the ultrasound transducers as being refracted. In the example of FIG. 3A, broken line indicates a route through which ultrasound waves are transmitted/received as being refracted. Besides, ultrasound waves are attenuated as having passed through the characteristic site CP.

The calculator 263 specifies the shape and the acoustic characteristics of the characteristic site CP with reference to the acoustic characteristics application data. The calculator 263 obtains a route UR for each of the ultrasound transducers using the shape and the acoustic characteristics thus specified and the general Snell's law. Then, the calculator 263 calculates delay time for each of the ultrasound transducers based on the entire length of the routes UR, part of the entire length over which ultrasound waves pass through the characteristic site CP, and the acoustic velocity of the characteristic site CP contained in the acoustic characteristics specified. Further, the calculator 263 calculates a weighting coefficient for each of the ultrasound transducers based on the entire length of the routes UR, part of the entire length over which ultrasound waves pass through the characteristic site CP, and the attenuation rate of the characteristic site CP contained in the acoustic characteristics specified. The calculator 263 calculates the delay time and the weighting coefficient with respect to each focal point FP in the scanning range SR.

The calculator 263 calculates the delay time and the weighting coefficient with respect to each focal point FP as well as each channel based on a positional relationship among the focal point FP, each of the ultrasound transducers and the characteristic site CP, and the shape and the acoustic characteristics of the characteristic site CP. For example, when the characteristic site CP has an arcuate shape and lies to form an arc projecting from the focal point FP side toward the ultrasound probe 1 side as illustrated in FIG. 3A, the delay time for the channel of the ultrasound transducer Ue is longer than that for the channel of the ultrasound transducer Ue illustrated in FIG. 3B. Besides, the weighting coefficient for the channel of the ultrasound transducer Ue illustrated in FIG. 3A is larger than that for the channel of the ultrasound transducer Ue illustrated in FIG. 3B.

The calculator 263 outputs the transmission/reception conditions thus calculated to the transceiver 21 and the signal processor 22. At this time, the calculator 263 feeds the transceiver 21 with the delay time calculated for each focal point as well as each channel. Further, the calculator 263 feeds the signal processor 22 with the delay time and the weighting coefficient calculated for each focal point as well as each channel. Thereby, the transmission/reception conditions are changed to the delay time and the weighting coefficient calculated. The transmission/reception conditions as used herein corresponds to operating conditions of the transceiver 21 and the signal processor 22. Examples of the transmission/reception conditions include the delay time and the weighting coefficient for transmitting and receiving ultrasound waves.

Described below is a process to generate ultrasound image data after the change of the transmission/reception conditions. The transceiver 21 outputs a pulse signal at a timing delayed by the delay time obtained from the calculator 263 for each channel to make the ultrasound probe 1 transmit ultrasound waves. With this, transmission beam forming is performed based on the transmission/reception conditions changed by the transmission/reception condition change unit 26.

The signal processor 22 performs delay processing and addition processing on the reception signal based on the delay time and the weighting coefficient obtained from the calculator 263. At this time, the signal processor 22 retrieves the reception signal from an address corresponding to the delay time obtained from the calculator 263. When the delay processors 222 include a small delay circuit, a delay time, which is less than the clock rate of the FIFO memories 221, may further be added to assign the delay time obtained from the calculator 263 to the reception signal.

The weighting processor 223 multiplies the reception signal that has assigned the delay time by the weighting coefficient obtained from the calculator 263 with respect to each channel. The weighting processor 223 outputs the reception signal multiplied by the weighting coefficient obtained from the calculator 263 to the adder 224. The adder 224 receives the reception signal from each of the weighting processors 223, and adds them up. This addition obtains the reception signal subjected to reception beam forming based on the transmission/reception conditions changed by the transmission/reception condition change unit 26.

The image generator 23 generates ultrasound image data based on the reception signal, on which the signal processor 22 has performed reception beam forming based on the transmission/reception conditions changed. This corresponds to that the image generator 23 generates ultrasound image data based on the transmission/reception conditions changed by the transmission/reception condition change unit 26. The image generator 23 outputs the ultrasound image data to the display controller 24.

As described above, based on the shape and the acoustic characteristics of the characteristic site included in the scanning range of ultrasound waves, the transmission/reception conditions of ultrasound waves are changed, thereby correcting the influence of refraction and attenuation of ultrasound waves due to the characteristic site. Besides, the characteristic site is specified based on the three-dimensional image data of the subject generated in advance. Thus, the transmission/reception conditions are changed in conformity with the characteristic site, the shape of which varies depending on each subject.

Incidentally, when the ultrasound probe 1 is a two-dimensional array probe, the transmission/reception condition change unit 26 changes the transmission/reception conditions related to the azimuth direction and the elevation direction (thickness direction). At this time, the acoustic characteristics application unit 262 three-dimensionally applies (reflects) the acoustic characteristics to a position represented by the characteristic site data. The calculator 263 calculates the transmission/reception conditions to be changed with respect to the azimuth and elevation directions, and outputs the conditions to the transceiver 21 and the signal processor 22.

As being operated by an operator such as a doctor or a technologist, the operation unit 4 feeds each unit of the apparatus with signals or information corresponding to the operation. The operation unit 4 includes, for example, a keyboard, a mouse, a touch panel, and the like.

The system controller 27 controls each unit of the ultrasound diagnosis apparatus. The system controller 27 stores in advance a computer program to implement the functions of each unit of the ultrasound diagnosis apparatus. The system controller 27 includes a processor to execute the computer program to thereby realize the above functions.

The term "processor" as used herein refers to a circuit such as central processing unit (CPU), graphical processing unit (GPU), application-specific integrated circuit (ASIC), programmable logic device (e.g., simple programmable logic device (SPLD), complex programmable logic device (CPLD), etc.), and field-programmable gate array (FPGA). The processor loads the stored program and executes it to implement the functions of each unit. The program may be directly incorporated in the circuit of the processor. In this case, the processor loads the program incorporated in the circuit and executes it, thereby implementing the functions of each unit. The processor need not necessarily be configured with a single circuit, and a plurality of independent circuits may be combined into one processor to implement the functions. Further, a plurality of functions may be integrated into one processor to implement the functions. For example, the system controller 27 stores a computer program related to the operation as described below and executes it.

FIG. 4 is a flowchart of the operation of the ultrasound diagnosis apparatus of the first embodiment.

Step S101: the reference image specifying unit 251 retrieves three-dimensional image data of the subject generated in advance from the medical image database 5.

Step S102: the transceiver 21 outputs a pulse signal to the ultrasound probe 1 to make the transceiver 21 transmit ultrasound waves. The transceiver 21 receives an echo signal from each of the ultrasound transducers of the ultrasound probe 1. The transceiver 21 converts the echo signal to a digital signal (reception signal) with respect to each channel, and outputs it to the signal processor 22. The signal processor 22 performs delay processing and addition processing on the reception signal received from the transceiver 21, thereby obtaining the reception signal subjected to phasing (i.e., subjected to reception beam forming). The signal processor 22 outputs the reception signal subjected to reception beam forming to the image generator 23. The image generator 23 generates ultrasound image data based on the reception signal from the signal processor 22. To the ultrasound image data generated in this step S102, the acoustic characteristics of the characteristic site are not applied (reflected) as illustrated in an example of FIG. 3B. That is, the ultrasound image data is generated based on transmission/reception conditions determined such that the acoustic velocity and the attenuation rate are uniform in the scanning range.

Step S103: the reference image specifying unit 251 receives the ultrasound image data from the image generator 23. The reference image specifying unit 251 performs registration between the ultrasound image data and the three-dimensional image data. Then, the reference image specifying unit 251 specifies reference image data from the three-dimensional image data. The reference image specifying unit 251 outputs the reference image data thus specified and the ultrasound image data to the site specifying unit 252.

Step S104: the site specifying unit 252 extracts a site having specific acoustic characteristics from the reference image data received from the reference image specifying unit 251. The site specifying unit 252 correlates the site having specific acoustic characteristics with the scanning range related to the ultrasound image data, thereby specifying a site included in the scanning range in the site extracted. The site specifying unit 252 outputs characteristic site data that represents the position and the shape of the characteristic site thus specified and the ultrasound image data to the transmission/reception condition change unit 26.

Step S105: the acoustic characteristics application unit 262 receives the characteristic site data and the ultrasound image data from the site specifying unit 252. The acoustic characteristics application unit 262 retrieves acoustic characteristics per unit length from the acoustic characteristics storage 261. The acoustic characteristics application unit 262 applies (reflects) the acoustic characteristics per unit length to the position (the position of the characteristic site) represented by the characteristic site data. The acoustic characteristics application unit 262 outputs acoustic characteristics application data, in which the acoustic characteristics of the characteristic site are applied to the scanning range of the ultrasound image data, to the calculator 263.

Step S106: the calculator 263 calculates the transmission/reception conditions to be changed based on the acoustic characteristics application data from the acoustic characteristics application unit 262. The calculator 263 specifies the shape and the acoustic characteristics of the characteristic site CP with reference to the acoustic characteristics application data. The calculator 263 obtains a route UR for each of the ultrasound transducers using the shape and the acoustic characteristics thus specified and the general Snell's law. Then, the calculator 263 calculates delay time and a weighting coefficient for each of the ultrasound transducers. The calculator 263 calculates the delay time and the weighting coefficient with respect to each focal point FP in the scanning range. The calculator 263 outputs the delay time calculated for each focal point as well as each channel to the transceiver 21, and the delay time and the weighting coefficient calculated for each focal point as well as each channel to the signal processor 22. Thereby, the transmission/reception conditions are changed to the delay time and the weighting coefficient calculated.

Step S107: the transceiver 21 outputs a pulse signal at a timing delayed by the delay time obtained from the calculator 263 for each channel to make the ultrasound probe 1 transmit ultrasound waves. The signal processor 22 performs delay processing and addition processing on the reception signal based on the delay time and the weighting coefficient obtained from the calculator 263. The image generator 23 generates ultrasound image data based on the reception signal, on which the signal processor 22 has performed reception beam forming based on the transmission/reception conditions changed. The image generator 23 outputs the ultrasound image data to the display controller 24.

Step S108: upon receipt of the ultrasound image data from the image generator 23, the display controller 24 displays, on the display 3, an ultrasound image based on the ultrasound image data.

According to the first embodiment, the ultrasound diagnosis apparatus is configured to change the transmission/reception conditions of ultrasound waves based on the shape and the acoustic characteristics of the characteristic site in the scanning range of ultrasound waves. Thus, the influence of refraction of ultrasound waves can be corrected, resulting in an improvement in the image quality of the ultrasound image.

Further, according to the first embodiment, the ultrasound diagnosis apparatus is configured to specify the characteristic site based on three-dimensional image data of the subject generated in advance. Therefore, the transmission/reception conditions are changed in conformity with the characteristic site, the shape of which varies depending on each subject. Thus, the influence of refraction of ultrasound waves can be corrected correspondingly to each subject.

Modification of the First Embodiment

A description is given of an ultrasound diagnosis apparatus according to a modification of the first embodiment. The ultrasound diagnosis apparatus of the modification is configured to allow the transmission/reception conditions to be changed manually. In the following, the differences from the ultrasound diagnosis apparatus of the first embodiment are mainly described. The same description as has already been provided may not be repeated.

The operator provides an input to newly change the transmission/reception conditions by operating the operation unit 4. For example, the operator operates the operation unit 4 to provide the input while viewing an ultrasound image displayed on the display 3. This input is intended to increase or decrease the acoustic characteristics (acoustic velocity, attenuation rate, etc.) applied (reflected) by the acoustic characteristics application unit 262. The transmission/reception condition change unit is fed with an operation signal that represents the input provided through the operation unit 4 via the system controller 27.

The transmission/reception condition change unit newly changes the transmission/reception conditions based on the input. At this time, the acoustic characteristics application unit 262 receives the operation signal from the system controller 27, and specifies which acoustic characteristic is to be increased or decreased and also how much it is to be increased or decreased, i.e., acoustic characteristic to be increased or decreased and increase or decrease amount. The acoustic characteristics application unit 262 increases or decreases the acoustic characteristic thus specified based on the increase or decrease amount. The acoustic characteristics application unit 262 outputs new acoustic characteristics application data, in which the acoustic characteristic is increased or decreased, to the calculator 263.

The calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed.

The transceiver 21 transmits/receives ultrasound waves via the ultrasound probe 1 based on the transmission/reception conditions newly changed. The signal processor 22 performs reception beam forming based on the transmission/reception conditions newly changed. The image generator 23 generates new ultrasound image data based on the transmission/reception conditions newly changed. The image generator 23 outputs the new ultrasound image data to the display controller 24. The display controller 24 displays, on the display 3, an ultrasound image based on the new ultrasound image data from the image generator 23.

Figure 5:
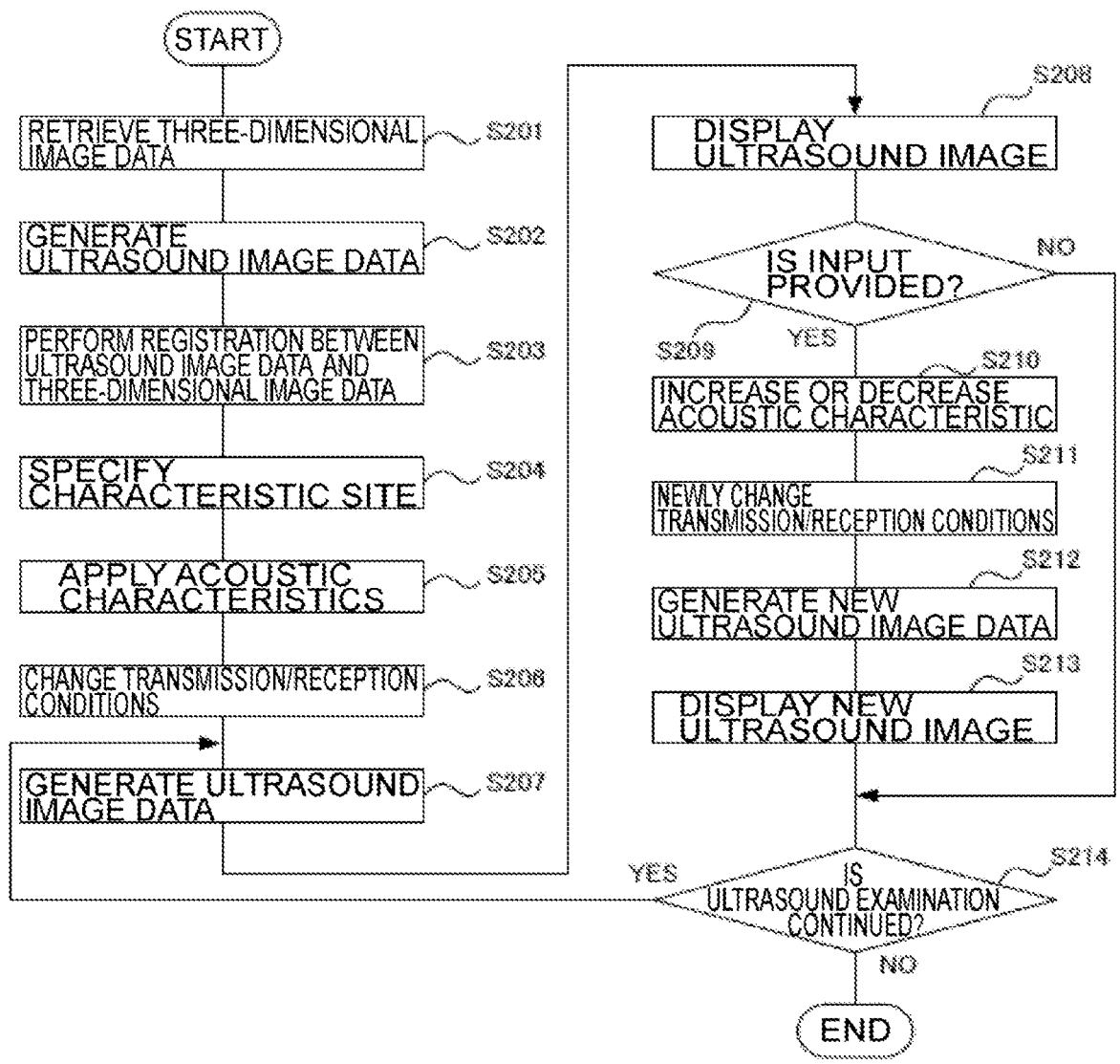
FIG. 5 is a flowchart of the operation of an ultrasound diagnosis apparatus according to a modification of the first embodiment.

FIG. 5 is a flowchart of the operation of the ultrasound diagnosis apparatus according to the modification of the first embodiment.

Steps S201 to S208 are the same as steps S101 to S108 described above in connection with FIG. 4.

Step S209: when an input is provided through the operation unit 4 to newly change the transmission/reception conditions (YES in step S209), the transmission/reception condition change unit is fed with an operation signal that represents the input provided through the operation unit 4 via the system controller 27. When no input is provided (NO in step S209), the process moves to step S214.

Step S210: the acoustic characteristics application unit 262 receives the operation signal from the system controller 27, and specifies an acoustic characteristic to be increased or decreased and an increase or decrease amount based on the operation signal. The acoustic characteristics application unit 262 increases or decreases the acoustic characteristic thus specified based on the increase or decrease amount. The acoustic characteristics application unit 262 outputs new acoustic characteristics application data, in which the acoustic characteristic is increased or decreased, to the calculator 263.

Step S211: the calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed.

Step S212: the transceiver 21 transmits/receives ultrasound waves via the ultrasound probe 1 based on the transmission/reception conditions newly changed. The signal processor 22 performs reception beam forming based on the transmission/reception conditions newly changed. The image generator 23 generates new ultrasound image data based on the transmission/reception conditions newly changed. The image generator 23 outputs the new ultrasound image data to the display controller 24.

Step S213: the display controller 24 displays, on the display 3, an ultrasound image based on the new ultrasound image data from the image generator 23.

Step S214: when the ultrasound examination is to be continued (YES in step S214), the process loops back to step S207. If not (NO in step S214), the process ends.

According to the modification of the first embodiment, the ultrasound diagnosis apparatus is configured to allow the transmission/reception conditions, which is applied (reflected) depending on the characteristic site, to be changed manually. This means that the operator can adjust the image quality of the ultrasound image based on the ultrasound image data generated according to the transmission/reception conditions, which have been changed based on the acoustic characteristics of the characteristic site per unit length stored in advance. Thus, the influence of refraction of ultrasound waves can be further corrected, resulting in a further improvement in the image quality of the ultrasound image.

Second Embodiment

A description is given of an ultrasound diagnosis apparatus according to a second embodiment. The ultrasound diagnosis apparatus of the second embodiment is configured to allow the transmission/reception conditions to be newly changed automatically. In the following, the differences from the ultrasound diagnosis apparatus of the first embodiment are mainly described. The same description as has already been provided may not be repeated.

Figure 6:
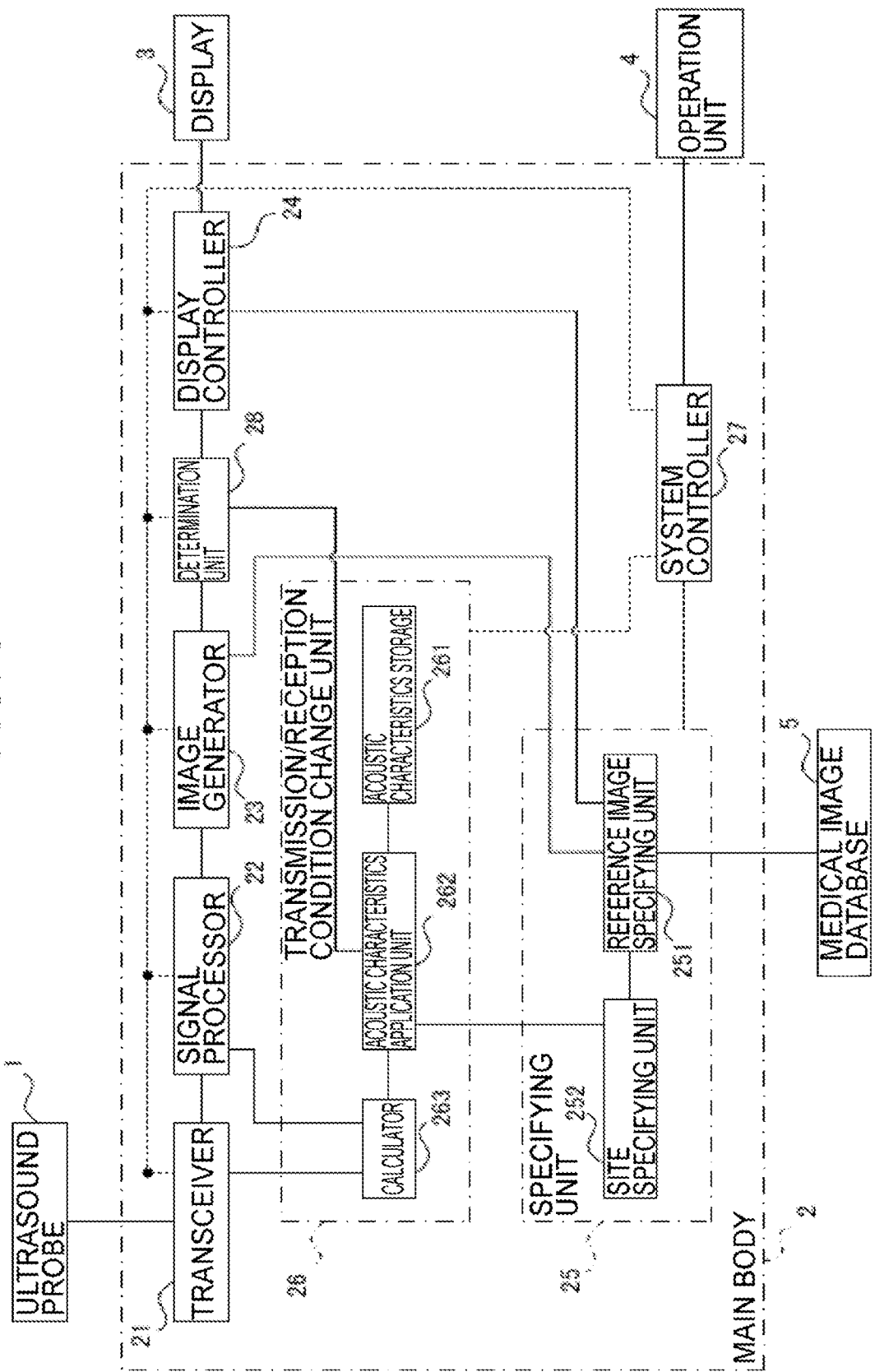
FIG. 6 is a block diagram illustrating the configuration of an ultrasound diagnosis apparatus according to a second embodiment.

FIG. 6 is a block diagram illustrating the configuration of the ultrasound diagnosis apparatus according to the second embodiment. The image generator 23 generates ultrasound image data based on the transmission/reception conditions changed by the transmission/reception condition change unit 26. The image generator 23 outputs the ultrasound image data thus generated to a determination unit 28. The image generator 23 may output the ultrasound image data to the display controller 24.

The main body 2 further includes the determination unit 28. The determination unit 28 determines whether to newly change the transmission/reception conditions based on the contrast of the ultrasound image data. For example, the determination unit 28 stores a predetermined contrast threshold in advance. The contrast threshold is provided by the operator in advance. The contrast threshold may include an upper limit value and a lower limit value. The determination unit 28 calculates the contrast of the ultrasound image data from the image generator 23 using a common calculation method as appropriate.

The determination unit 28 compares the contrast thus calculated with the contrast threshold. For example, when the contrast is equal to or higher than the contrast threshold, the determination unit 28 determines to newly change the transmission/reception conditions. When the contrast is less than the contrast threshold, the determination unit 28 determines not to change the transmission/reception conditions. Incidentally, the determination unit 28 may determine to newly change the transmission/reception conditions when the contrast is higher than the contrast threshold and not to change the conditions when the contrast is equal to or less than the threshold.

If the contrast threshold includes an upper limit value and a lower limit value, the determination unit 28 determines to newly change the transmission/reception conditions when the contrast is not in between the upper limit value and the lower limit value. The determination unit 28 determines not to change the transmission/reception conditions when the contrast falls in between the upper limit value and the lower limit value. Having determined to newly change the transmission/reception conditions, the determination unit 28 outputs difference data that represents the difference between the contrast and the contrast threshold to the acoustic characteristics application unit 262. Having determined not to change the transmission/reception conditions, the determination unit 28 outputs the ultrasound image data to the display controller 24.

The acoustic characteristics application unit 262 increases or decreases an acoustic characteristic based on the difference data from the determination unit 28. This increase or decrease process may be performed by using a general contrast control algorithm. The acoustic characteristics application unit 262 outputs new acoustic characteristics application data, in which acoustic characteristics thus changed are applied (reflected), to the calculator 263.

The calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed. Then, ultrasound image data is generated based on the new transmission/reception conditions. Having determined not to change the transmission/reception conditions, the determination unit 28 outputs the ultrasound image data to the display controller 24. The display controller 24 displays, on the display 3, an ultrasound image based on the ultrasound image data from the determination unit 28.

Figure 7:
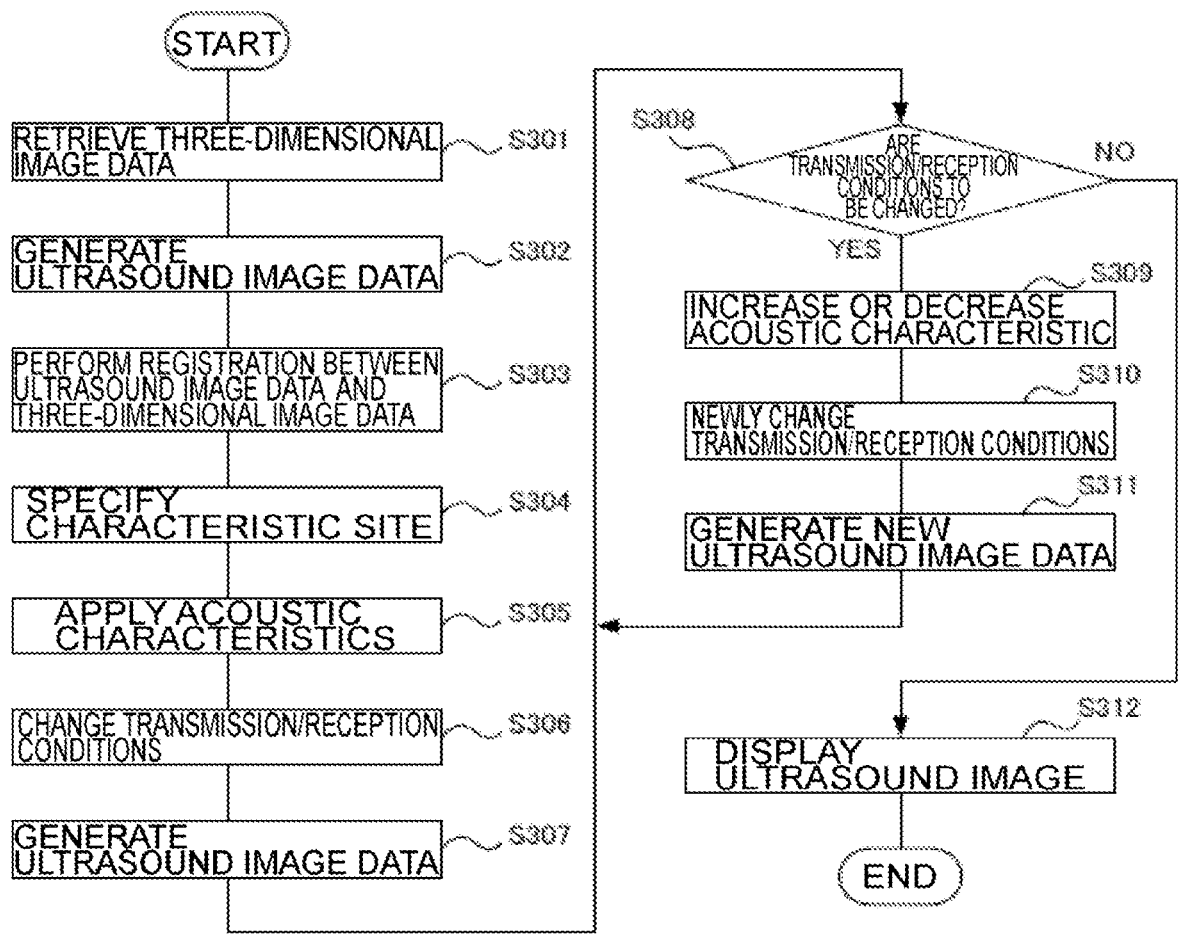
FIG. 7 is a flowchart of the operation of the ultrasound diagnosis apparatus of the second embodiment.

FIG. 7 is a flowchart of the operation of the ultrasound diagnosis apparatus of the second embodiment.

Steps S301 to S306 are the same as steps S101 to S106 described above in connection with FIG. 4.

Step S307: the image generator 23 generates ultrasound image data based on the transmission/reception conditions changed by the transmission/reception condition change unit 26. The image generator outputs the ultrasound image data thus generated to the determination unit 28.

Step S308: the determination unit 28 calculates the contrast of the ultrasound image data from the image generator 23. The determination unit 28 compares the contrast thus calculated with the contrast threshold to determine whether to newly change the transmission/reception conditions. Having determined to newly change the transmission/reception conditions (YES in step S308), the determination unit 28 outputs difference data that represents the difference between the contrast and the contrast threshold to the acoustic characteristics application unit 262. Having determined not to change the transmission/reception conditions (NO in step S308), the determination unit 28 outputs the ultrasound image data to the display controller 24.

Step S309: the acoustic characteristics application unit 262 increases or decreases an acoustic characteristic based on the difference data from the determination unit 28. The acoustic characteristics application unit 262 outputs new acoustic characteristics application data, in which acoustic characteristics thus changed are applied (reflected), to the calculator 263.

Step S310: the calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed.

Step S311: the transceiver 21 transmits/receives ultrasound waves via the ultrasound probe 1 based on the transmission/reception conditions newly changed. The signal processor 22 performs reception beam forming based on the transmission/reception conditions newly changed. The image generator 23 generates new ultrasound image data based on the transmission/reception conditions newly changed. The image generator 23 outputs the new ultrasound image data to the determination unit 28.

After the new ultrasound image data is output to the determination unit 28, steps S309 to S311 are repeated until the determination unit 28 determines not to change the transmission/reception conditions.

Step S312: the display controller 24 displays, on the display 3, an ultrasound image based on the ultrasound image data from the image Generator 23.

According to the second embodiment, the ultrasound diagnosis apparatus is configured to allow the transmission/reception conditions, which is applied (reflected) depending on the characteristic site, to be changed automatically. This means to automatically determine and adjust the image quality of the ultrasound image based on the ultrasound image data generated according to the transmission/reception conditions, which have been changed based on the acoustic characteristics of the characteristic site per unit length stored in advance. Thus, the influence of refraction of ultrasound waves can be further corrected, resulting in a further improvement in the image quality of the ultrasound image.

Third Embodiment

A description is given of an ultrasound diagnosis apparatus according to a third embodiment. The ultrasound diagnosis apparatus of the third embodiment is configured to be capable of specifying a characteristic site while following the movement of the ultrasound probe 1. In the following, the differences from the ultrasound diagnosis apparatus of the first embodiment are mainly described. The same description as has already been provided may not be repeated.

Figure 8:
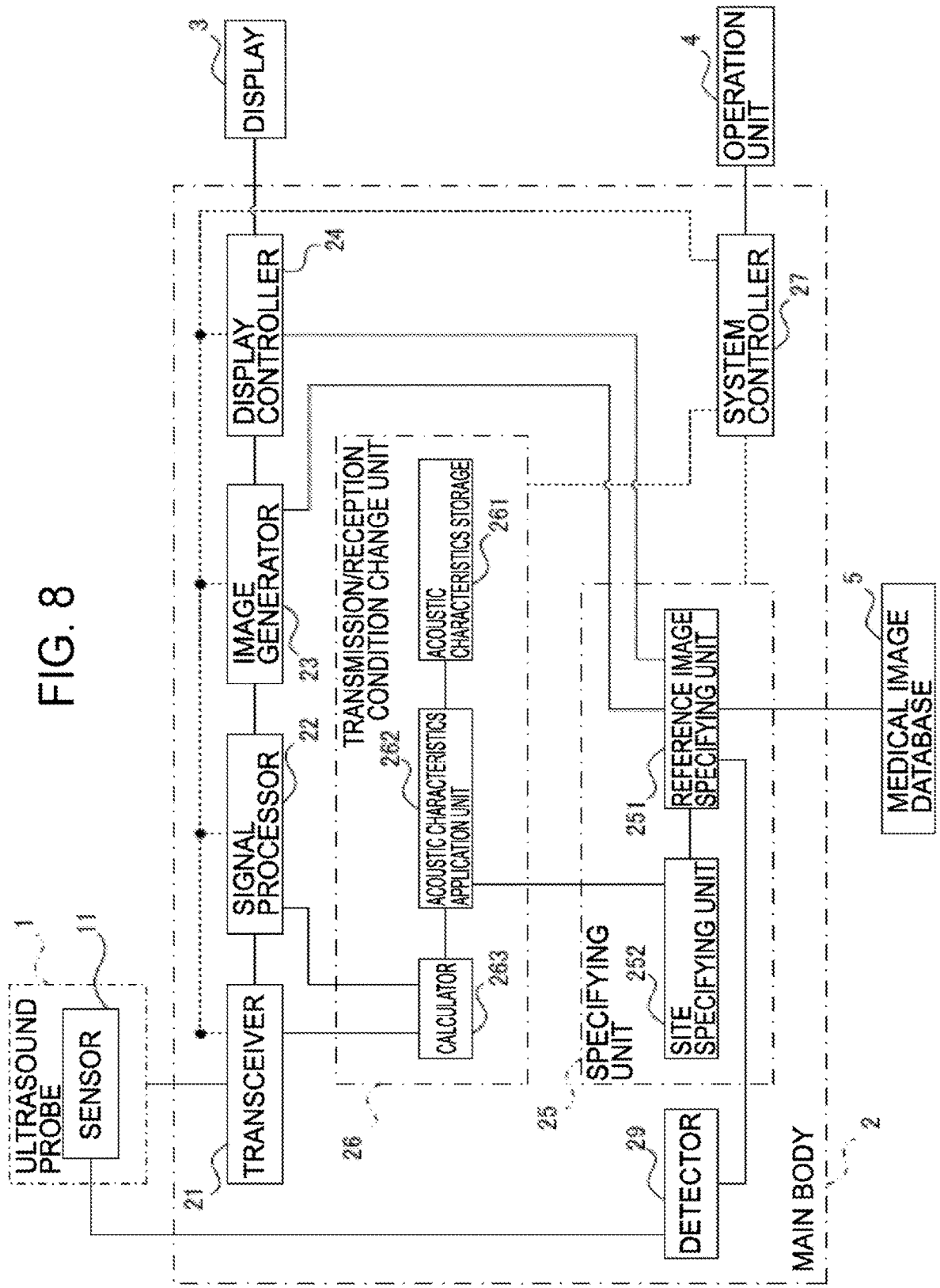
FIG. 8 is a block diagram illustrating the configuration of an ultrasound diagnosis apparatus according to a third embodiment.

FIG. 8 is a block diagram illustrating the configuration of the ultrasound diagnosis apparatus according to the third embodiment. The ultrasound probe 1 includes a sensor 11. The main body 2 further includes a detector 29. The sensor 11 and the detector 29 are communicably connected to each other.

The sensor 11 and the detector 29 are provided to be able to detect either or both the position and the angle of the ultrasound probe 1. As the sensor 11 and the detector 29, a magnetic sensor or an optical sensor and a detector compatible thereto are appropriately employed. Through the sensor 11, the detector 29 detects either or both the position and the angle of the ultrasound probe 1 at regular intervals. The detector 29 successively outputs position angle data that represents either or both the position and the angle of the ultrasound probe 1 thus detected to the reference image specifying unit 251.

When the position of the ultrasound probe 1 moves, the reference image specifying unit 251 newly specifies a characteristic site based on the position detected. For example, the reference image specifying unit 251 stores position angle data when ultrasound waves are transmitted/received to generate an ultrasound image that is registered to three-dimensional image data. This position angle data is hereinafter referred to as reference position angle data. The reference image specifying unit 251 compares position angle data received after storing the reference position angle data with the reference position angle data. With this comparison, the reference image specifying unit 251 determines whether the ultrasound probe 1 has moved.

Having determined that the ultrasound probe 1 has moved, the reference image specifying unit 251 specifies either or both the position and the angle of the ultrasound probe 1 after the ultrasound probe 1 has moved based on either or both the position and the angle of the ultrasound probe 1 represented by the position angle data when the determination is made. The reference image specifying unit 251 performs registration between either or both the position and the angle of the ultrasound probe 1 and three-dimensional image data. This registration achieves position matching between the three-dimensional image data and the ultrasound probe 1 that has moved. Thus, the coordinate system of the scanning range of ultrasound waves corresponds to that of the three-dimensional image data.

The reference image specifying unit 251 specifies, as new reference image data, image data having a plane of the scanning range of ultrasound waves as a cross section in the three-dimensional image data by MPR. The reference image specifying unit 251 outputs the new reference image data thus specified and scanning range data that represents the scanning range of ultrasound waves to the site specifying unit 252. Having determined that the ultrasound probe 1 has not moved, the reference image specifying unit 251 is in standby without specifying new reference image data.

The site specifying unit 252 specifies a new characteristic site, which is included in the scanning range of ultrasound waves, in the new reference image data based on the new reference image data and the scanning range data. The site specifying unit 252 outputs new characteristic site data that represents the position and the shape of the characteristic site newly specified and the scanning range data to the transmission/reception condition change unit 26.

The transmission/reception condition change unit 26 newly changes the transmission/reception conditions based on the acoustic characteristics of the characteristic site newly specified. For example, the acoustic characteristics application unit 262 receives the new characteristic site data and the scanning range data from the site specifying unit 252. Then, the acoustic characteristics application unit 262 retrieves the acoustic characteristics per unit length from the acoustic characteristics storage 261. The acoustic characteristics application unit 262 applies (reflects) the acoustic characteristics per unit length to the position (the position of the new characteristic site) represented by the new characteristic site data. The acoustic characteristics application unit 262 outputs new acoustic characteristics application data, in which the acoustic characteristics of the new characteristic site are applied (reflected) to the scanning range, to the calculator 263.

The calculator 263 calculates the transmission/reception conditions to be newly changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are changed to those newly calculated.

As described above, even if the ultrasound probe 1 is moved, a new characteristic site is specified in the scanning range of ultrasound waves after the movement to newly apply (reflect) the acoustic characteristics. Thus, the transmission/reception conditions can be changed following the movement of the ultrasound probe 1. Thus, even in an ultrasound examination in which the ultrasound probe 1 is moved, the influence of refraction of ultrasound waves can be corrected, resulting in an improvement in the image quality of the ultrasound image.

Figure 9:
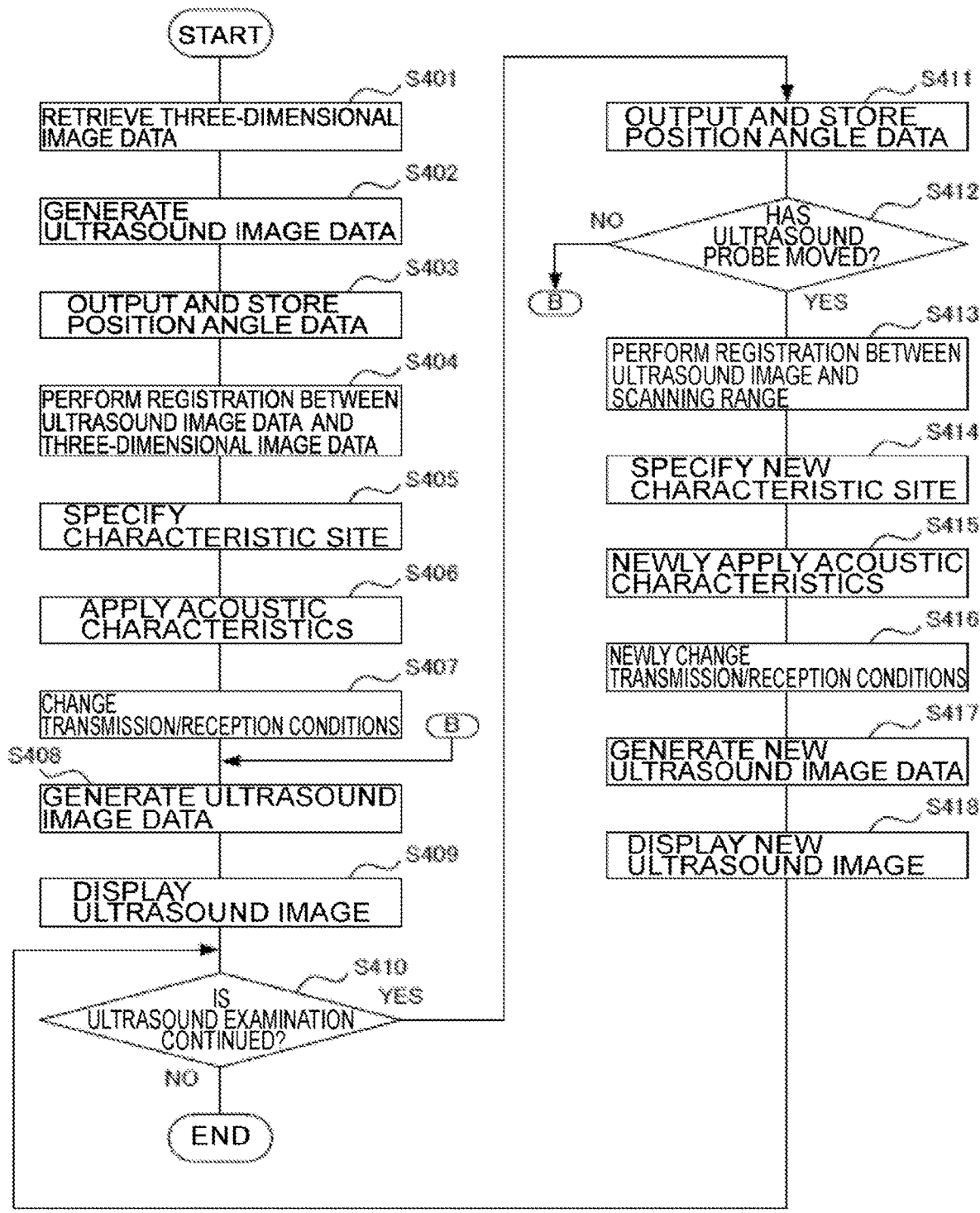
FIG. 9 is a flowchart of the operation of the ultrasound diagnosis apparatus of the third embodiment.

FIG. 9 is a flowchart of the operation of the ultrasound diagnosis apparatus of the third embodiment.

Steps S401 and S402 are the same as steps S101 and S102 described above in connection with FIG. 4.

Step S403: the detector 29 detects either or both the position and the angle of the ultrasound probe 1 through the sensor 11. The detector 29 outputs position angle data that represents either or both the position and the angle of the ultrasound probe 1 thus detected to the reference image specifying unit 251. The reference image specifying unit 251 stores the position angle data (reference position angle data).

Steps S404 to S409 are the same as steps S103 to S108 described above in connection with FIG. 4.

Step S410: when the ultrasound examination is to be continued (YES in step S410), the process moves to step S411. If not (NO in step S410), the process ends.

Step S411: the detector 29 detects either or both the position and the angle of the ultrasound probe 1 through the sensor 11. The detector 29 outputs position angle data that represents either or both the position and the angle of the ultrasound probe 1 thus detected to the reference image specifying unit 251.

Step S412: the reference image specifying unit 251 compares the position angle data received after storing the reference position angle data with the reference position angle data. With this comparison, the reference image specifying unit 251 determines whether the ultrasound probe 1 has moved. Having determined that the ultrasound probe 1 has moved (YES in step S412), the reference image specifying unit 251 specifies either or both the position and the angle of the ultrasound probe 1 after the ultrasound probe 1 has moved based on either or both the position and the angle of the ultrasound probe 1 represented by the position angle data when the determination is made. Having determined that the ultrasound probe 1 has not moved (NO in step S412), the process returns to step S408. Thus, steps S408 to S411 are repeated until the ultrasound probe 1 is moved during the ultrasound examination.

Step S413: the reference image specifying unit 251 performs registration between either or both the position and the angle of the ultrasound probe 1 and three-dimensional image data. The reference image specifying unit 251 specifies, as new reference image data, image data having a plane of the scanning range of ultrasound waves as a cross section in the three-dimensional image data by MPR. The reference image specifying unit 251 outputs the new reference image data thus specified and scanning range data that represents the scanning range of ultrasound waves to the site specifying unit 252.

Step S414: the site specifying unit 252 specifies a new characteristic site, which is included in the scanning range of ultrasound waves, in the new reference image data based on the new reference image data and the scanning range data from the reference image specifying unit 251. The site specifying unit 252 outputs new characteristic site data that represents the position and the shape of the characteristic site newly specified and the scanning range data to the transmission/reception condition change unit 26.

Step S415: the acoustic characteristics application unit 262 receives the new characteristic site data and the scanning range data from the site specifying unit 252. Then, the acoustic characteristics application unit 262 retrieves the acoustic characteristics per unit length from the acoustic characteristics storage 261. The acoustic characteristics application unit 262 applies (reflects) the acoustic characteristics per unit length to the position (the position of the new characteristic site) represented by the new characteristic site data. The acoustic characteristics application unit 262 outputs new acoustic characteristics application data, in which the acoustic characteristics of the new characteristic site are applied (reflected) to the scanning range, to the calculator 263.

Step S416: the calculator 263 calculates the transmission/reception conditions to be newly changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are changed to those newly calculated.

Step S417: the transceiver 21 transmits/receives ultrasound waves via the ultrasound probe 1 based on the transmission/reception conditions newly changed. The signal processor 22 performs reception beam forming based on the transmission/reception conditions newly changed. The image generator 23 generates new ultrasound image data based on the transmission/reception conditions newly changed. The image generator 23 outputs the new ultrasound image data to the display controller 24.

Step S418: the display controller 24 displays, on the display 3, an ultrasound image based on the new ultrasound image data. The, the process loops back to step S410. Thus, steps S410 to S418 are repeated. This corresponds to that the transmission/reception conditions are successively changed following the movement of the ultrasound probe 1 and thereby ultrasound image data is successively generated.

According to the third embodiment, even if the ultrasound probe 1 is moved, a new characteristic site is specified in the scanning range of ultrasound waves after the movement to newly apply (reflect) the acoustic characteristics. Thus, the transmission/reception conditions can be changed following the movement of the ultrasound probe 1. Thus, even in an ultrasound examination in which the ultrasound probe 1 is moved, the influence of refraction of ultrasound waves can be corrected, resulting in an improvement in the image quality of the ultrasound image.

Modification of the Third Embodiment

A description is given of an ultrasound diagnosis apparatus according to a modification of the third embodiment. The ultrasound diagnosis apparatus of the modification is configured to allow the transmission/reception conditions to be changed manually. In the following, the differences from the ultrasound diagnosis apparatus of the third embodiment are mainly described. The same description as has already been provided may not be repeated.

The operator provides an input to newly change the transmission/reception conditions by operating the operation unit 4. For example, the operator operates the operation unit 4 to provide the input while viewing an ultrasound image displayed on the display 3. This input is intended to increase or decrease the acoustic characteristics (acoustic velocity, attenuation rate, etc.) applied (reflected) by the acoustic characteristics application unit 262. The transmission/reception condition change unit is fed with an operation signal that represents the input provided through the operation unit 4 via the system controller 27.

The transmission/reception condition change unit newly changes the transmission/reception conditions based on the input. At this time, the acoustic characteristics application unit 262 receives the operation signal from the system controller 27, and specifies which acoustic characteristic is to be increased or decreased and also how much it is to be increased or decreased, i.e., acoustic characteristic to be increased or decreased and increase or decrease amount. The acoustic characteristics application unit 262 increases or decreases the acoustic characteristic thus specified based on the increase or decrease amount. The acoustic characteristics application unit 262 outputs new acoustic characteristics application data, in which the acoustic characteristic is increased or decreased, to the calculator 263.

The calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed.

Figure 10:
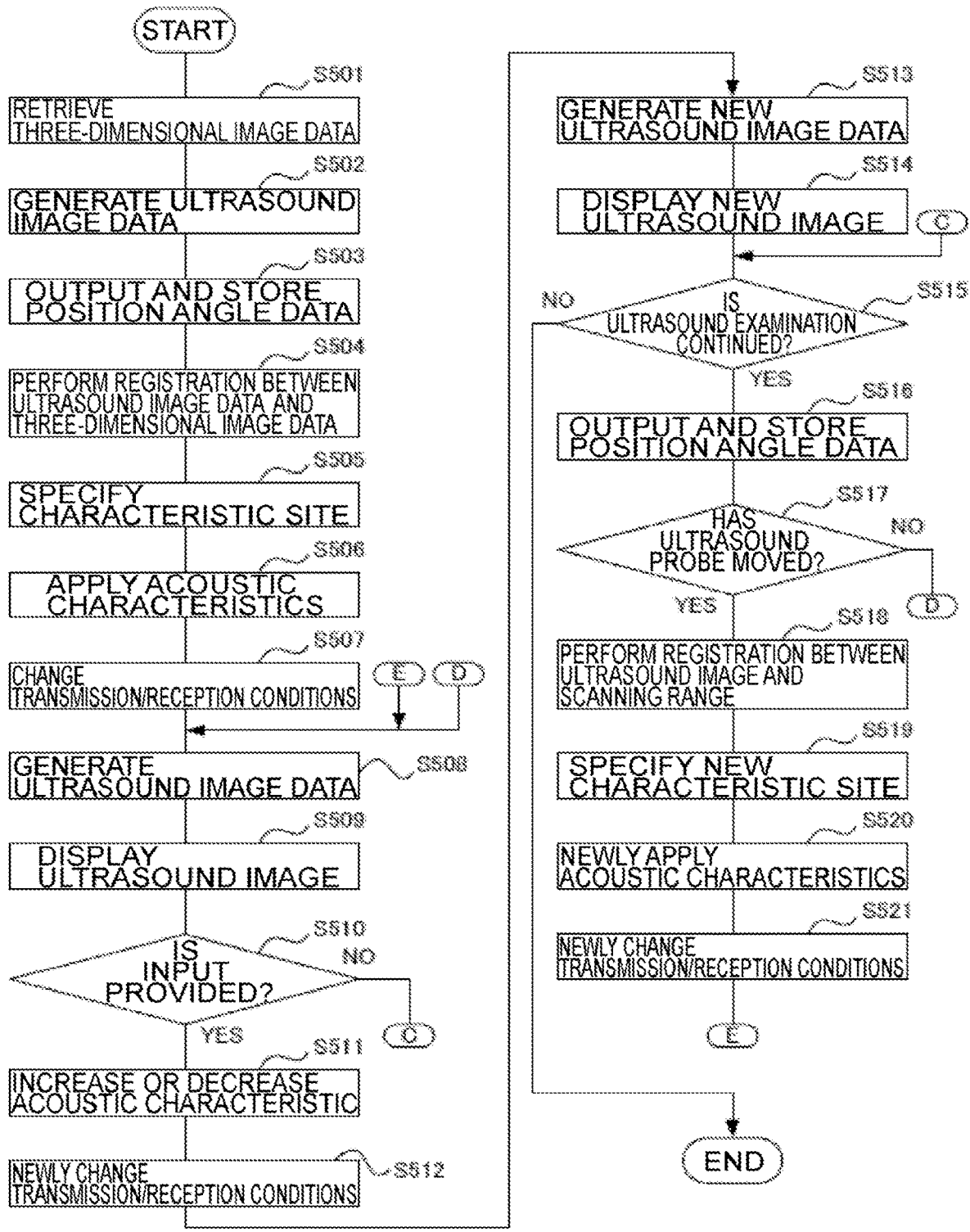
FIG. 10 is a flowchart of the operation of an ultrasound diagnosis apparatus according to a modification of the third embodiment.

FIG. 10 is a flowchart of the operation of the ultrasound diagnosis apparatus according to the modification of the third embodiment.

Steps S501 to S509 are the same as steps S401 to S409 in FIG. 4.

Step S510: when an input is provided through the operation unit 4 to newly change the transmission/reception conditions (YES in step S510), the transmission/reception condition change unit is fed with an operation signal that represents the input provided through the operation unit 4 via the system controller 27. When no input is provided (NO in step S510), the process moves to step S515.

Step S511: the acoustic characteristics application unit 262 receives the operation signal from the system controller 27, and specifies an acoustic characteristic to be increased or decreased and an increase or decrease amount based on the operation signal. The acoustic characteristics application unit 262 increases or decreases the acoustic characteristic thus specified based on the increase or decrease amount. The acoustic characteristics application unit 262 outputs new acoustic characteristics application data, in which the acoustic characteristic is increased or decreased, to the calculator 263.

Step S512: the calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed.

Step S513: the transceiver 21 transmits/receives ultrasound waves via the ultrasound probe 1 based on the transmission/reception conditions newly changed. The signal processor 22 performs reception beam forming based on the transmission/reception conditions newly changed. The image generator 23 generates new ultrasound image data based on the transmission/reception conditions newly changed. The image generator 23 outputs the new ultrasound image data to the display controller 24.

Step S514: the display controller 24 displays, on the display 3, an ultrasound image based on the new ultrasound image data from the image generator 23.

Step S515: when the ultrasound examination is to be continued (YES in step S515), the process moves to step S516. If not (NO in step S515), the process ends.

Step S516: the detector 29 detects either or both the position and the angle of the ultrasound probe 1 through the sensor 11. The detector 29 outputs position angle data that represents either or both the position and the angle of the ultrasound probe 1 thus detected to the reference image specifying unit 251.

Step S517: the reference image specifying unit 251 compares the position angle data received after storing the reference position angle data with the reference position angle data. With this comparison, the reference image specifying unit 251 determines whether the ultrasound probe 1 has moved. Having determined that the ultrasound probe 1 has moved (YES in step S517), the reference image specifying unit 251 specifies either or both the position and the angle of the ultrasound probe 1 after the ultrasound probe 1 has moved based on either or both the position and the angle of the ultrasound probe 1 represented by the position angle data when the determination is made. Having determined that the ultrasound probe 1 has not moved (NO in step S517), the process returns to step S508. Thus, steps S508 to S516 are repeated while the ultrasound probe 1 is stationary during the ultrasound examination.

Step S518: the reference image specifying unit 251 performs registration between either or both the position and the angle of the ultrasound probe 1 and three-dimensional image data. The reference image specifying unit 251 specifies, as new reference image data, image data having a plane of the scanning range of ultrasound waves as a cross section in the three-dimensional image data by MPR. The reference image specifying unit 251 outputs the new reference image data thus specified and scanning range data that represents the scanning range of ultrasound waves to the site specifying unit 252.

Step S519: the site specifying unit 252 specifies a new characteristic site, which is included in the scanning range of ultrasound waves, in the new reference image data based on the new reference image data and the scanning range data from the reference image specifying unit 251. The site specifying unit 252 outputs new characteristic site data that represents the position and the shape of the characteristic site newly specified and the scanning range data to the transmission/reception condition change unit 26.

Step S520: the acoustic characteristics application unit 262 receives the new characteristic site data and the scanning range data from the site specifying unit 252. Then, the acoustic characteristics application unit 262 retrieves the acoustic characteristics per unit length from the acoustic characteristics storage 261. The acoustic characteristics application unit 262 applies (reflects) the acoustic characteristics per unit length to the position (the position of the new characteristic site) represented by the new characteristic site data. The acoustic characteristics application unit 262 outputs new acoustic characteristics application data, in which the acoustic characteristics of the new characteristic site are applied (reflected) to the scanning range, to the calculator 263.

Step S521: the calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed.

According to the modification of the third embodiment, even if the ultrasound probe 1 is moved, a new characteristic site is specified in the scanning range of ultrasound waves after the movement to newly apply (reflect) the acoustic characteristics. Thus, the transmission/reception conditions can be changed following the movement of the ultrasound probe 1. Besides, the ultrasound diagnosis apparatus of this modification is configured to allow the acoustic characteristics, which is applied (reflected) depending on the characteristic site, to be changed manually. This means that the operator can adjust the image quality of the ultrasound image based on the ultrasound image data generated according to the transmission/reception conditions, which have been changed based on the acoustic characteristics of the characteristic site per unit length stored in advance. Thus, even in an ultrasound examination in which the ultrasound probe 1 is moved, the influence of refraction of ultrasound waves can be further corrected, resulting in a further improvement in the image quality of the ultrasound image.

Fourth Embodiment

A description is given of an ultrasound diagnosis apparatus according to a fourth embodiment. The ultrasound diagnosis apparatus of the fourth embodiment is configured to allow the transmission/reception conditions to be newly changed automatically. In the following, the differences from the ultrasound diagnosis apparatus of the third embodiment are mainly described. The same description as has already been provided may not be repeated.

Figure 11:
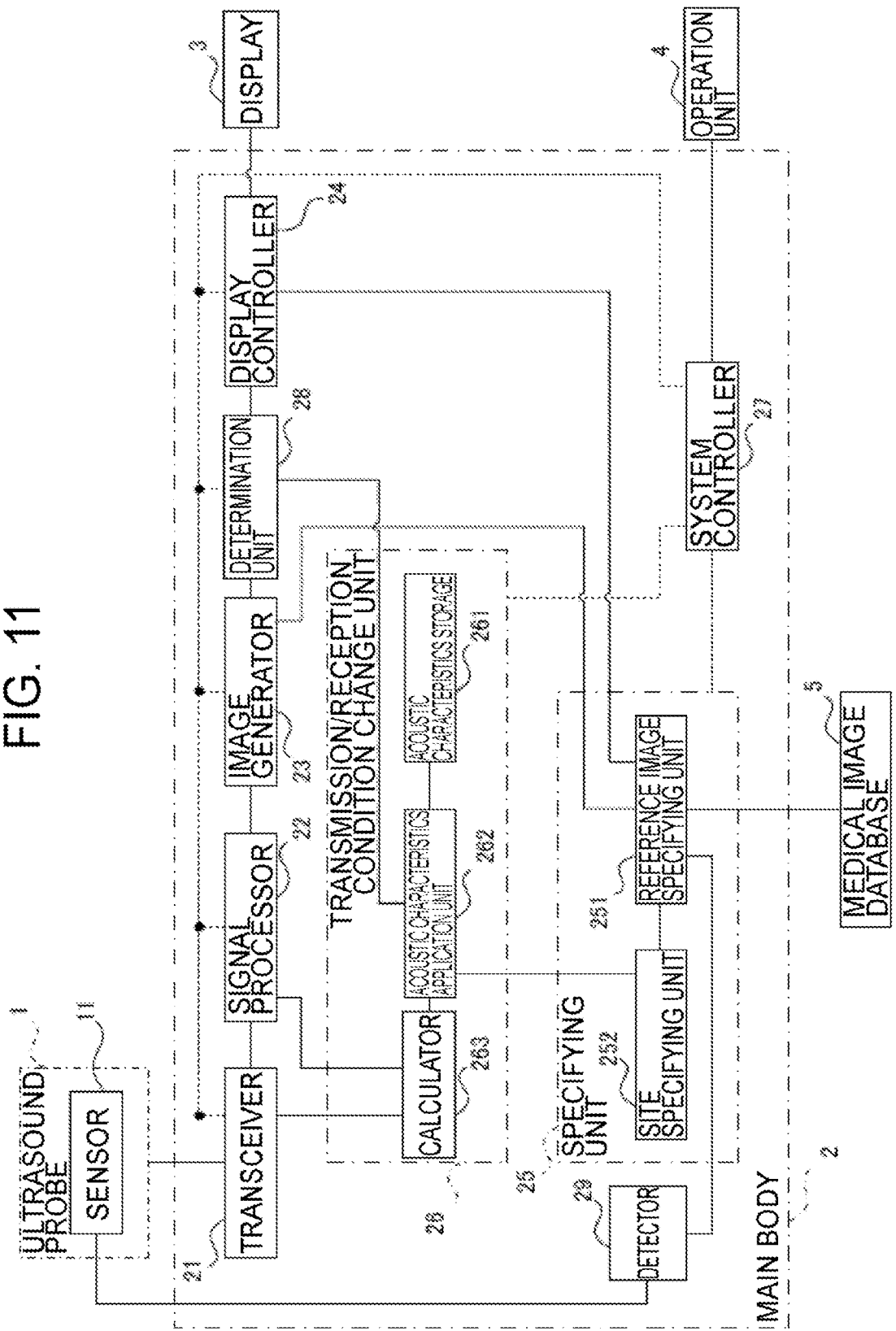
FIG. 11 is a block diagram illustrating the configuration of an ultrasound diagnosis apparatus according to a fourth embodiment.

FIG. 11 is a block diagram illustrating the configuration of the ultrasound diagnosis apparatus according to the fourth embodiment. The image generator 23 generates ultrasound image data based on the transmission/reception conditions changed by the transmission/reception condition change unit 26. The image generator outputs the ultrasound image data thus generated to the determination unit 28. The image generator 23 may output the ultrasound image data to the display controller 24.

The main body 2 further includes the determination unit 28. The determination unit 28 determines whether to newly change the transmission/reception conditions based on the contrast of the ultrasound image data. For example, the determination unit 28 stores a predetermined contrast threshold in advance. The contrast threshold is provided by the operator in advance. The contrast threshold may include an upper limit value and a lower limit value. The determination unit 28 calculates the contrast of the ultrasound image data from the image generator 23 using a common calculation method as appropriate.

The determination unit 28 compares the contrast thus calculated with the contrast threshold. For example, when the contrast is equal to or higher than the contrast threshold, the determination unit 28 determines to newly change the transmission/reception conditions. When the contrast is less than the contrast threshold, the determination unit 28 determines not to change the transmission/reception conditions. Incidentally, the determination unit 28 may determine to newly change the transmission/reception conditions when the contrast is higher than the contrast threshold and not to change the conditions when the contrast is equal to or less than the threshold.

If the contrast threshold includes an upper limit value and a lower limit value, the determination unit 28 determines to newly change the transmission/reception conditions when the contrast is not in between the upper limit value and the lower limit value. The determination unit 28 determines not to change the transmission/reception conditions when the contrast falls in between the upper limit value and the lower limit value. Having determined to newly change the transmission/reception conditions, the determination unit 28 outputs difference data that represents the difference between the contrast and the contrast threshold to the acoustic characteristics application unit 262. Having determined not to change the transmission/reception conditions, the determination unit 28 outputs the ultrasound image data to the display controller 24.

The acoustic characteristics application unit 262 increases or decreases an acoustic characteristic based on the difference data from the determination unit 28. This increase or decrease process may be performed by using a general contrast control algorithm. The acoustic characteristics application unit 262 outputs new acoustic characteristics application data, in which acoustic characteristics thus changed are applied (reflected), to the calculator 263.

The calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed. Then, ultrasound image data is generated based on the new transmission/reception conditions. Having determined not to change the transmission/reception conditions, the determination unit 28 outputs the ultrasound image data to the display controller 24. The display controller 24 displays, on the display 3, an ultrasound image based on the ultrasound image data from the determination unit 28.

Figure 12:
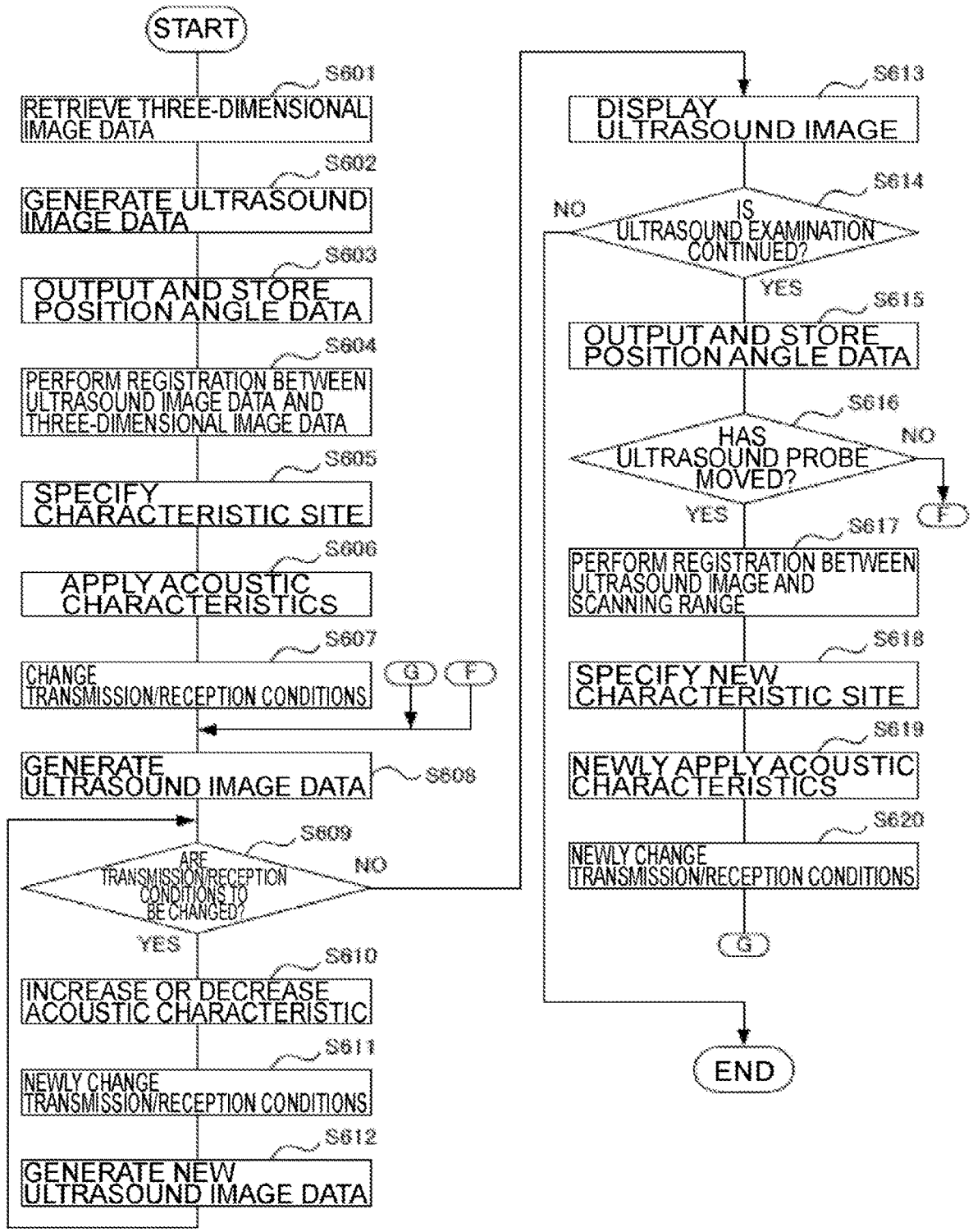
FIG. 12 is a flowchart of the operation of the ultrasound diagnosis apparatus of the fourth embodiment.

FIG. 12 is a flowchart of the operation of the ultrasound diagnosis apparatus of the fourth embodiment.

Steps S601 to S608 are the same as steps S401 to S408 in FIG. 4.

Step S609: the determination unit 28 calculates the contrast of the ultrasound image data from the image generator 23. The determination unit 28 compares the contrast thus calculated with the contrast threshold to determine whether to newly change the transmission/reception conditions. Having determined to newly change the transmission/reception conditions (YES in step S609), the determination unit 28 outputs difference data that represents the difference between the contrast and the contrast threshold to the acoustic characteristics application unit 262. Having determined not to change the transmission/reception conditions (NO in step S609), the determination unit 28 outputs the ultrasound image data to the display controller 24.

Step S610: the acoustic characteristics application unit 262 increases or decreases an acoustic characteristic based on the difference data from the determination unit 28. The acoustic characteristics application unit 262 outputs new acoustic characteristics application data, in which acoustic characteristics thus changed are applied (reflected), to the calculator 263.

Step S611: the calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed.

Step S612: the transceiver 21 transmits/receives ultrasound waves via the ultrasound probe 1 based on the transmission/reception conditions newly changed. The signal processor 22 performs reception beam forming based on the transmission/reception conditions newly changed. The image generator 23 generates new ultrasound image data based on the transmission/reception conditions newly changed. The image generator 23 outputs the new ultrasound image data to the determination unit 28.

After the new ultrasound image data is output to the determination unit 28, steps S610 to S612 are repeated until the determination unit 28 determines not to change the transmission/reception conditions.

Step S613: the display controller 24 displays, on the display 3, an ultrasound image based on the ultrasound image data from the image Generator 23.

Step S614: when the ultrasound examination is to be continued (YES in step S614), the process moves to step S615. If not (NO in step S614), the process ends.

Step S615: the detector 29 detects either or both the position and the angle of the ultrasound probe 1 through the sensor 11. The detector 29 outputs position angle data that represents either or both the position and the angle of the ultrasound probe 1 thus detected to the reference image specifying unit 251.

Step S616: the reference image specifying unit 251 compares the position angle data received after storing the reference position angle data with the reference position angle data. With this comparison, the reference image specifying unit 251 determines whether the ultrasound probe 1 has moved. Having determined that the ultrasound probe 1 has moved (YES in step S616), the reference image specifying unit 251 specifies either or both the position and the angle of the ultrasound probe 1 after the ultrasound probe 1 has moved based on either or both the position and the angle of the ultrasound probe 1 represented by the position angle data when the determination is made. Having determined that the ultrasound probe 1 has not moved (NO in step S616), the process returns to step S608. Thus, steps S608 to S615 are repeated while the ultrasound probe 1 is stationary during the ultrasound examination.

Step S617: the reference image specifying unit 251 performs registration between either or both the position and the angle of the ultrasound probe 1 and three-dimensional image data. The reference image specifying unit 251 specifies, as new reference image data, image data having a plane of the scanning range of ultrasound waves as a cross section in the three-dimensional image data by MPR. The reference image specifying unit 251 outputs the new reference image data thus specified and scanning range data that represents the scanning range of ultrasound waves to the site specifying unit 252.

Step S618: the site specifying unit 252 specifies a new characteristic site, which is included in the scanning range of ultrasound waves, in the new reference image data based on the new reference image data and the scanning range data from the reference image specifying unit 251. The site specifying unit 252 outputs new characteristic site data that represents the position and the shape of the characteristic site newly specified and the scanning range data to the transmission/reception condition change unit 26.

Step S619: the acoustic characteristics application unit 262 receives the new characteristic site data and the scanning range data from the site specifying unit 252. Then, the acoustic characteristics application unit 262 retrieves the acoustic characteristics per unit length from the acoustic characteristics storage 261. The acoustic characteristics application unit 262 applies (reflects) the acoustic characteristics per unit length to the position (the position of the new characteristic site) represented by the new characteristic site data. The acoustic characteristics application unit 262 outputs new acoustic characteristics application data, in which the acoustic characteristics of the new characteristic site are applied (reflected) to the scanning range, to the calculator 263.

Step S620: the calculator 263 newly calculates the transmission/reception conditions to be changed based on the new acoustic characteristics application data from the acoustic characteristics application unit 262. The calculator 263 outputs the transmission/reception conditions thus calculated to the transceiver 21 and the signal processor 22. Thereby, the transmission/reception conditions are newly changed.

According to the fourth embodiment, even if the ultrasound probe 1 is moved, a new characteristic site is specified in the scanning range of ultrasound waves after the movement to newly apply (reflect) the acoustic characteristics. Thus, the transmission/reception conditions can be changed following the movement of the ultrasound probe 1. Besides, the ultrasound diagnosis apparatus of the fourth embodiment is configured to allow the transmission/reception conditions, which is applied (reflected) depending on the characteristic site, to be changed automatically. This means to automatically determine and adjust the image quality of the ultrasound image based on the ultrasound image data generated according to the transmission/reception conditions, which have been changed based on the acoustic characteristics of the characteristic site per unit length stored in advance. Thus, even in an ultrasound examination in which the ultrasound probe 1 is moved, the influence of refraction of ultrasound waves can be further corrected, resulting in a further improvement in the image quality of the ultrasound image.

According to at least one of the above embodiments, the transmission/reception conditions are changed depending on a characteristic site. Thereby, the influence of refraction of ultrasound waves can be corrected, resulting in an improvement in the image quality of the ultrasound image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus configured to generate ultrasound image data of a subject through an ultrasound probe, the ultrasound diagnosis apparatus comprising processing circuitry configured to:
specify a characteristic site, which is included in a scanning range related to the ultrasound image data and has specific acoustic characteristics, based on three-dimensional image data of the subject generated in advance;
obtain a weighting coefficient based on an attenuation rate of the characteristic site;
obtain a delay time based on the acoustic characteristics of the characteristic site;
change reception conditions of ultrasound waves by multiplying each of reception signals, which has been delayed by the delay time, by the weighting coefficient with respect to each channel, and adding up the reception signals to obtain a reception signal that has been subjected to reception beam forming; and
generate the ultrasound image data based on the reception signal that has been subjected to reception beam forming under changed reception conditions.

2. The ultrasound diagnosis apparatus of claim 1, further comprising a detector configured to detect either or both position and angle of the ultrasound probe,
wherein the processing circuitry is further configured to:
specify a new characteristic site based on the position and the angle of the ultrasound probe when the ultrasound probe has moved; and
change the reception conditions based on acoustic characteristics of the new characteristic site.

3. The ultrasound diagnosis apparatus of claim 1, wherein the processing circuitry is further configured to:
determine whether to newly change the reception conditions based on contrast of the ultrasound image data; and
change the reception conditions when reception conditions are determined to be changed.

4. The ultrasound diagnosis apparatus of claim 1, further comprising an operation unit configured to receive an input to newly change the reception conditions,
wherein the processing circuitry is further configured to change the reception conditions based on the input.

5. The ultrasound diagnosis apparatus of claim 1, wherein the ultrasound probe is a two-dimensional array probe, and
the processing circuitry is further configured to change the reception conditions related to azimuth direction and elevation direction of the two-dimensional array probe.

6. The ultrasound diagnosis apparatus of claim 1, wherein the three-dimensional image data is generated by at least one of an X-ray CT apparatus, an MRI apparatus, an ultrasound diagnosis apparatus, and an X-ray diagnosis apparatus.

7. The ultrasound diagnosis apparatus of claim 1, wherein the characteristic site is a site including bone.

8. The ultrasound diagnosis apparatus of claim 7, wherein the site including bone is skull.

9. The ultrasound diagnosis apparatus of claim 1, wherein
the processing circuitry is further configured to specify reference image data in the three-dimensional image data of the subject generated in advance, the reference image data corresponding to the scanning range of the ultrasound image data; and
the characteristic site in the ultrasound image data is specified based on the reference image data specified in the three-dimensional image.

10. The ultrasound diagnosis apparatus of claim 9, wherein
the processing circuitry is further configured to extract the characteristic site from the reference image data, and
the characteristic site in the ultrasound image data is specified based on the characteristic site extracted from the reference image data.

11. The ultrasound diagnosis apparatus of claim 10, wherein
the processing circuitry is further configured to specify a shape of the characteristic site in the ultrasound image data based on the extracted characteristic site, and
the reception conditions of ultrasound waves are changed by obtaining the weighting coefficient and delay time based on the shape and the acoustic characteristics of the characteristic site.

12. The ultrasound diagnosis apparatus of claim 1, wherein the ultrasound probe includes ultrasound transducers,
the processing circuitry is further configured to obtain for each of the ultrasound transducers a route between the ultrasound transducer and a focal point in the scanning range, based on the acoustic characteristics of the characteristic site; and
the reception conditions of ultrasound waves are changed by obtaining the weighting coefficient and delay time based on the route and the acoustic characteristics of the characteristic site.

* * * * *